(12) United States Patent
Chu et al.

(10) Patent No.: US 10,449,018 B2
(45) Date of Patent: Oct. 22, 2019

(54) GINGIVAL OVATE PONTIC AND METHODS OF USING THE SAME

(71) Applicants: Stephen J. Chu, New York, NY (US); Jocelyn Huiping Tan-Chu, New York, NY (US)

(72) Inventors: Stephen J. Chu, New York, NY (US); Jocelyn Huiping Tan-Chu, New York, NY (US)

( * ) Notice: Subject to any disclaimer, the term of this patent is extended or adjusted under 35 U.S.C. 154(b) by 0 days.

(21) Appl. No.: 15/064,122

(22) Filed: Mar. 8, 2016

(65) Prior Publication Data

US 2016/0262854 A1  Sep. 15, 2016

Related U.S. Application Data

(60) Provisional application No. 62/130,074, filed on Mar. 9, 2015.

(51) Int. Cl.
*A61C 8/00* (2006.01)
*A61C 8/02* (2006.01)

(52) U.S. Cl.
CPC ............ *A61C 8/008* (2013.01); *A61C 8/0006* (2013.01)

(58) Field of Classification Search
CPC .. A61C 13/10; A61C 8/00; A61C 8/08; A61C 8/0006
See application file for complete search history.

(56) References Cited

U.S. PATENT DOCUMENTS

| | | |
|---|---|---|
| 2,253,222 A | 8/1941 | Bertram |
| 3,430,344 A | 3/1969 | Sekendur |
| RE27,227 E | 11/1971 | Harnsberger |
| 3,906,634 A | 9/1975 | Aspel |
| 3,909,855 A | 10/1975 | Barredo |
| 3,919,772 A | 11/1975 | Lenczycki |
| 3,958,471 A | 5/1976 | Muller |
| 4,011,602 A | 3/1977 | Rybicki |

(Continued)

FOREIGN PATENT DOCUMENTS

| | | |
|---|---|---|
| DE | 10029256 | 11/2000 |
| EP | 0 747 017 | 12/1996 |

(Continued)

OTHER PUBLICATIONS

International Search Report and Written Opinion from International Application No. PCT/US2016/021393 dated Jul. 25, 2016.

(Continued)

*Primary Examiner* — Nicholas D Lucchesi
(74) *Attorney, Agent, or Firm* — Nixon Peabody LLP

(57) ABSTRACT

A pontic device for preserving soft tissue in a tooth-extraction site includes a generally curved apical end. The apical end has a first perimeter and is configured to rest in a tooth extraction socket and substantially conform to soft tissue of a tooth-extraction site immediately after a tooth has been extracted. The pontic device further includes an opposing, generally concave coronal end. The coronal end has a second perimeter that is configured to substantially correspond to and form a seal with gingival tissue surrounding the tooth-extraction site. The coronal end is configured to receive a tooth-shaped coronal pontic portion to form a final restoration.

11 Claims, 7 Drawing Sheets

(56) References Cited

U.S. PATENT DOCUMENTS

| | | |
|---|---|---|
| 4,056,585 A | 11/1977 | Waltke |
| 4,086,701 A | 5/1978 | Kawahara |
| 4,172,323 A | 10/1979 | Orlowski |
| 4,177,562 A | 12/1979 | Miller |
| 4,229,170 A | 10/1980 | Perez |
| 4,269,595 A | 5/1981 | Nemethy |
| 4,294,544 A | 10/1981 | Altschuler |
| 4,306,862 A | 12/1981 | Knox |
| 4,307,044 A | 12/1981 | Perez |
| 4,310,312 A | 1/1982 | Keller et al. |
| 4,325,373 A | 4/1982 | Slivenko |
| 4,332,564 A | 6/1982 | Lord |
| 4,341,312 A | 7/1982 | Scholer |
| 4,346,750 A | 8/1982 | Nemethy |
| 4,364,381 A | 12/1982 | Sher |
| 4,380,432 A | 4/1983 | Orlowski et al. |
| 4,396,054 A | 8/1983 | Cole |
| 4,439,152 A | 3/1984 | Small |
| 4,445,862 A | 5/1984 | Chiaramonte et al. |
| 4,457,714 A | 7/1984 | Klein |
| 4,543,953 A | 10/1985 | Slocum |
| 4,547,157 A | 10/1985 | Driskell |
| 4,571,180 A | 2/1986 | Kulick |
| 4,611,288 A | 9/1986 | Duret |
| 4,624,673 A | 11/1986 | Meyer |
| 4,663,720 A | 5/1987 | Duret |
| 4,689,013 A | 8/1987 | Lustig |
| 4,690,643 A | 9/1987 | Rousseau |
| 4,693,686 A | 9/1987 | Sendax |
| 4,704,089 A | 11/1987 | Shoher et al. |
| 4,713,004 A | 12/1987 | Linkow |
| 4,713,005 A | 12/1987 | Marshall et al. |
| 4,756,689 A | 7/1988 | Lundgren |
| 4,758,161 A | 7/1988 | Niznick |
| 4,758,162 A | 7/1988 | Dobbs |
| 4,764,116 A | 8/1988 | Shoher et al. |
| 4,767,331 A | 8/1988 | Hoe |
| 4,772,204 A | 9/1988 | Soderberg |
| 4,775,320 A | 10/1988 | Marshall et al. |
| 4,813,873 A | 3/1989 | Seaton |
| 4,820,157 A | 4/1989 | Salvo |
| 4,821,200 A | 4/1989 | Öberg |
| 4,842,518 A | 6/1989 | Linkow |
| 4,850,870 A | 7/1989 | Lazzara |
| 4,850,873 A | 7/1989 | Lazzara |
| 4,854,872 A | 8/1989 | Detsch |
| 4,856,994 A | 8/1989 | Lazzara |
| 4,872,839 A | 10/1989 | Brajnovic |
| 4,877,400 A | 10/1989 | Holsclaw |
| 4,906,191 A | 3/1990 | Soderberg |
| 4,906,420 A | 3/1990 | Brajnovic |
| 4,931,016 A | 6/1990 | Sillard |
| 4,935,635 A | 6/1990 | O'Harra |
| 4,955,811 A | 9/1990 | Lazzara et al. |
| 4,957,439 A | 9/1990 | Shoher et al. |
| 4,961,674 A | 10/1990 | Wang |
| 4,964,770 A | 10/1990 | Steinbichler |
| 4,986,753 A | 1/1991 | Sellers |
| 4,988,297 A | 1/1991 | Lazzara |
| 4,988,298 A | 1/1991 | Lazzara |
| 4,998,881 A | 3/1991 | Lauks |
| 5,000,685 A | 3/1991 | Brajnovic |
| 5,000,687 A | 3/1991 | Yarovesky et al. |
| 5,006,069 A | 4/1991 | Lazzara |
| 5,015,183 A | 5/1991 | Fenick |
| 5,015,186 A | 5/1991 | Detsch |
| 5,030,096 A | 7/1991 | Hurson |
| 5,035,619 A | 7/1991 | Daftary |
| 5,040,982 A | 8/1991 | Stefan-Dogar |
| 5,040,983 A | 8/1991 | Binon |
| 5,064,375 A | 11/1991 | Jörnéus |
| 5,071,351 A | 12/1991 | Green, Jr. |
| 5,073,111 A | 12/1991 | Daftary |
| 5,074,791 A | 12/1991 | Shoher et al. |
| 5,087,200 A | 2/1992 | Brajnovic |
| 5,100,323 A | 3/1992 | Friedman |
| 5,104,318 A | 4/1992 | Piche |
| 5,106,300 A | 4/1992 | Voitik |
| 5,120,224 A | 6/1992 | Golub |
| 5,122,059 A | 6/1992 | Dürr |
| 5,125,839 A | 6/1992 | Ingber |
| 5,125,841 A | 6/1992 | Carlsson |
| 5,133,660 A | 7/1992 | Fenick |
| 5,135,395 A | 8/1992 | Marlin |
| 5,145,371 A | 9/1992 | Jörnéus |
| 5,145,372 A | 9/1992 | Daftary |
| 5,176,516 A | 1/1993 | Koizumi |
| 5,186,626 A | 2/1993 | Tanaka |
| 5,188,800 A | 2/1993 | Green, Jr. |
| 5,195,892 A | 3/1993 | Gersberg |
| 5,205,745 A | 4/1993 | Kamiya |
| 5,209,659 A | 5/1993 | Friedman |
| 5,209,666 A | 5/1993 | Balfour |
| 5,213,502 A | 5/1993 | Daftary |
| 5,221,204 A | 6/1993 | Kruger |
| 5,237,998 A | 8/1993 | Duret |
| 5,246,370 A | 9/1993 | Coatoam |
| 5,257,184 A | 10/1993 | Mushabac |
| 5,281,140 A | 1/1994 | Niznick |
| 5,286,195 A | 2/1994 | Clostermann |
| 5,286,196 A | 2/1994 | Brajnovic |
| 5,292,252 A | 3/1994 | Nickerson |
| 5,297,963 A | 3/1994 | Dafatry |
| 5,302,125 A | 4/1994 | Kownacki |
| 5,312,254 A | 5/1994 | Rosenlicht |
| 5,312,409 A | 5/1994 | McLaughlin |
| 5,316,476 A | 5/1994 | Krauser |
| 5,320,529 A | 6/1994 | Pompa |
| 5,328,371 A | 7/1994 | Hund |
| 5,333,898 A | 8/1994 | Stutz |
| 5,334,024 A | 8/1994 | Niznick |
| 5,336,090 A | 8/1994 | Wilson, Jr. |
| 5,338,196 A | 8/1994 | Beaty |
| 5,338,198 A | 8/1994 | Wu |
| 5,343,391 A | 8/1994 | Mushabac |
| 5,344,457 A | 9/1994 | Pilliar |
| 5,350,297 A | 9/1994 | Cohen |
| 5,359,511 A | 10/1994 | Schroeder |
| 5,362,234 A | 11/1994 | Salazar |
| 5,362,235 A | 11/1994 | Daftary |
| 5,368,483 A | 11/1994 | Sutter |
| 5,370,692 A | 12/1994 | Fink |
| 5,372,502 A | 12/1994 | Massen |
| 5,386,292 A | 1/1995 | Massen |
| 5,413,481 A | 5/1995 | Göppel |
| 5,417,568 A | 5/1995 | Diglio |
| 5,417,569 A | 5/1995 | Perisse |
| 5,417,570 A | 5/1995 | Zuest |
| 5,419,702 A | 5/1995 | Beaty |
| 5,431,567 A | 7/1995 | Datary |
| 5,433,606 A | 7/1995 | Niznick et al. |
| 5,437,551 A | 8/1995 | Chalifoux |
| 5,440,393 A | 8/1995 | Wenz |
| 5,452,219 A | 9/1995 | Dehoff |
| 5,458,488 A | 10/1995 | Chalifoux |
| 5,476,382 A | 12/1995 | Daftary |
| 5,476,383 A | 12/1995 | Beaty |
| 5,492,471 A | 2/1996 | Singer |
| 5,516,288 A | 5/1996 | Sichler |
| 5,527,182 A | 6/1996 | Willoughby |
| 5,533,898 A | 7/1996 | Mena |
| 5,538,426 A | 7/1996 | Harding |
| 5,547,377 A | 8/1996 | Daftary |
| 5,556,278 A | 9/1996 | Meitner |
| 5,561,675 A | 10/1996 | Bayon et al. |
| 5,564,921 A | 10/1996 | Marlin |
| 5,564,924 A | 10/1996 | Kwan |
| 5,569,578 A | 10/1996 | Mushabac |
| 5,571,016 A | 11/1996 | Ingber et al. |
| 5,575,656 A | 11/1996 | Hajjar |
| 5,580,244 A | 12/1996 | White |
| 5,580,246 A | 12/1996 | Fried |
| 5,595,703 A | 1/1997 | Swaelens |
| 5,599,185 A | 2/1997 | Greenberg |

(56) References Cited

U.S. PATENT DOCUMENTS

| | | |
|---|---|---|
| 5,613,832 A | 3/1997 | Su |
| 5,613,852 A | 3/1997 | Bavitz |
| 5,613,854 A | 3/1997 | Sweatt |
| 5,630,717 A | 5/1997 | Zuest |
| 5,636,986 A | 6/1997 | Prezeshkian |
| 5,651,675 A | 7/1997 | Singer |
| 5,652,709 A | 7/1997 | Andersson |
| 5,658,147 A | 8/1997 | Phimmasone |
| 5,662,476 A | 9/1997 | Ingber |
| 5,674,069 A | 10/1997 | Osorio |
| 5,674,071 A | 10/1997 | Beaty |
| 5,674,073 A | 10/1997 | Ingber |
| 5,681,167 A | 10/1997 | Lazarof |
| 5,685,714 A | 11/1997 | Beaty et al. |
| 5,685,715 A | 11/1997 | Beaty |
| 5,688,283 A | 11/1997 | Knapp |
| 5,704,936 A | 1/1998 | Mazel |
| 5,718,579 A | 2/1998 | Kennedy |
| 5,725,376 A | 3/1998 | Poirier |
| 5,733,124 A | 3/1998 | Kwan |
| 5,741,215 A | 4/1998 | Fink |
| 5,743,916 A | 4/1998 | Greenberg |
| 5,759,036 A * | 6/1998 | Hinds .................. A61C 8/005 433/172 |
| 5,762,125 A | 6/1998 | Mastrorio |
| 5,762,500 A | 6/1998 | Lazarof |
| 5,768,134 A | 6/1998 | Swaelens |
| 5,769,636 A | 6/1998 | Di Sario |
| 5,779,481 A | 7/1998 | Aires |
| 5,791,902 A | 8/1998 | Lauks |
| 5,800,168 A | 9/1998 | Cascione |
| 5,810,589 A | 9/1998 | Michnick et al. |
| 5,810,592 A * | 9/1998 | Daftary ................ A61C 8/005 433/172 |
| 5,813,858 A | 9/1998 | Singer |
| 5,823,778 A | 10/1998 | Schmitt |
| 5,842,859 A | 12/1998 | Palacci |
| 5,846,079 A | 12/1998 | Knode |
| 5,851,115 A | 12/1998 | Carlsson |
| 5,857,853 A | 1/1999 | Van Nifterick |
| 5,871,358 A | 2/1999 | Ingber |
| 5,873,722 A | 2/1999 | Lazzara |
| 5,876,204 A | 3/1999 | Day |
| 5,885,078 A | 3/1999 | Cagna |
| 5,888,034 A | 3/1999 | Greenberg |
| 5,888,068 A | 3/1999 | Lans et al. |
| 5,890,902 A * | 4/1999 | Sapian ................ A61C 8/0048 433/173 |
| 5,899,695 A | 5/1999 | Lazzara et al. |
| 5,899,697 A | 5/1999 | Lazzara et al. |
| 5,904,483 A | 5/1999 | Wade |
| 5,915,962 A | 6/1999 | Rosenlicht |
| 5,927,982 A | 7/1999 | Kruger |
| 5,931,675 A | 8/1999 | Callan |
| 5,934,907 A | 8/1999 | Marshall |
| 5,938,443 A | 8/1999 | Lazzara |
| 5,947,732 A | 9/1999 | Beaty et al. |
| 5,954,769 A | 9/1999 | Rosenlicht |
| 5,964,591 A | 10/1999 | Beaty |
| 5,967,777 A | 10/1999 | Klein |
| 5,984,681 A | 11/1999 | Huang |
| 5,984,682 A | 11/1999 | Carlson |
| 5,989,025 A | 11/1999 | Conley |
| 5,989,026 A | 11/1999 | Rogers et al. |
| 5,989,029 A * | 11/1999 | Osorio .................. A61C 8/005 433/173 |
| 5,989,258 A | 11/1999 | Hattori |
| 5,997,681 A | 12/1999 | Kinzie |
| 6,000,939 A | 12/1999 | Ray |
| 6,008,905 A | 12/1999 | Breton |
| 6,013,105 A | 1/2000 | Potts |
| 6,030,219 A | 2/2000 | Zuest et al. |
| 6,039,569 A | 3/2000 | Prasad et al. |
| 6,049,743 A | 4/2000 | Baba |
| 6,050,820 A | 4/2000 | Lans et al. |
| 6,068,479 A | 5/2000 | Kwan |
| 6,099,311 A | 8/2000 | Wagner |
| 6,099,313 A | 8/2000 | Dorken |
| 6,099,314 A | 8/2000 | Kopelman |
| 6,120,293 A | 9/2000 | Lazzara |
| 6,129,548 A | 10/2000 | Lazzara |
| 6,135,773 A | 10/2000 | Lazzara |
| 6,142,782 A | 11/2000 | Lazarof |
| 6,152,737 A | 11/2000 | Beaty et al. |
| 6,164,969 A | 12/2000 | Dinkelacker |
| 6,168,435 B1 | 1/2001 | Beaty et al. |
| 6,174,168 B1 | 1/2001 | Dehoff |
| 6,175,413 B1 | 1/2001 | Lucas |
| 6,190,169 B1 | 2/2001 | Bluemli |
| 6,296,483 B1 | 2/2001 | Champleboux |
| 6,197,410 B1 | 3/2001 | Vallittu |
| 6,200,125 B1 | 3/2001 | Akutagawa |
| 6,200,136 B1 | 3/2001 | Prasad et al. |
| 6,206,693 B1 | 3/2001 | Hultgren |
| 6,210,162 B1 | 4/2001 | Chishti |
| 6,217,334 B1 | 4/2001 | Hultgren |
| 6,227,857 B1 | 5/2001 | Morgan |
| 6,227,859 B1 | 5/2001 | Sutter |
| 6,250,925 B1 | 6/2001 | Marshall |
| 6,283,753 B1 * | 9/2001 | Willoughby .......... A61C 8/0001 433/172 |
| 6,287,117 B1 | 9/2001 | Niznick |
| 6,287,119 B1 | 9/2001 | van Nifterick |
| 6,299,449 B1 | 10/2001 | Carlson |
| 6,305,939 B1 | 10/2001 | Dawood |
| 6,312,259 B1 | 11/2001 | Kvarnstrom et al. |
| 6,319,000 B1 | 11/2001 | Branemark |
| 6,322,728 B1 | 11/2001 | Brodkin |
| 6,343,930 B1 | 2/2002 | Beaty et al. |
| 6,382,975 B1 | 5/2002 | Poirier |
| 6,386,876 B1 | 5/2002 | Lee |
| 6,402,707 B1 | 6/2002 | Ernst |
| 6,419,491 B1 | 7/2002 | Ricci et al. |
| 6,426,114 B1 | 7/2002 | Troczynski et al. |
| 6,428,803 B1 | 8/2002 | Ewers et al. |
| 6,431,866 B2 | 8/2002 | Hurson |
| 6,431,867 B1 | 8/2002 | Gittelson |
| 6,482,444 B1 | 11/2002 | Bellantone et al. |
| 6,488,503 B1 | 12/2002 | Lichkus |
| 6,497,573 B2 | 12/2002 | Wagner et al. |
| 6,497,574 B1 | 12/2002 | Miller |
| 6,537,069 B1 * | 3/2003 | Simmons, Jr. ......... A61C 8/001 433/173 |
| 6,540,784 B2 | 4/2003 | Barlow |
| 6,558,162 B1 | 5/2003 | Porter |
| 6,568,936 B2 | 5/2003 | MacDougald |
| 6,575,751 B1 | 6/2003 | Lehmann |
| 6,594,539 B1 | 7/2003 | Geng |
| 6,610,079 B1 | 8/2003 | Li |
| 6,619,958 B2 | 9/2003 | Beaty |
| 6,629,840 B2 | 10/2003 | Chishti |
| 6,634,883 B2 | 10/2003 | Ranalli |
| 6,644,970 B1 | 11/2003 | Lin |
| 6,648,640 B2 | 11/2003 | Rubbert |
| 6,663,387 B2 | 12/2003 | Riley |
| 6,663,388 B1 | 12/2003 | Schär et al. |
| 6,671,539 B2 | 12/2003 | Gateno |
| 6,672,870 B2 | 1/2004 | Knapp |
| 6,688,887 B2 | 2/2004 | Morgan |
| 6,691,764 B2 | 2/2004 | Embert |
| 6,743,491 B2 | 6/2004 | Cirincione |
| 6,755,652 B2 | 6/2004 | Nanni |
| D493,890 S * | 8/2004 | Schulter ................ D24/156 |
| 6,772,026 B2 | 8/2004 | Bradbury |
| 6,776,614 B2 | 8/2004 | Wiechmann |
| 6,783,359 B2 | 8/2004 | Kapit |
| 6,790,035 B2 | 9/2004 | Tricca et al. |
| 6,790,040 B2 | 9/2004 | Amber |
| 6,793,491 B2 | 9/2004 | Klein |
| 6,808,659 B2 | 10/2004 | Schulman |
| 6,814,575 B2 | 11/2004 | Poirier |
| 6,821,462 B2 | 11/2004 | Schulamn |
| 6,829,498 B2 | 12/2004 | Kipke |
| D503,804 S | 4/2005 | Phleps |

(56) References Cited

U.S. PATENT DOCUMENTS

| | | | |
|---|---|---|---|
| 6,882,894 B2 | 4/2005 | Durbin | |
| 6,885,464 B1 | 4/2005 | Pfeiffer | |
| 6,902,401 B2 | 6/2005 | Jorneus | |
| D507,052 S | 7/2005 | Wohrle | |
| 6,913,463 B2 | 7/2005 | Blacklock | |
| 6,926,442 B2 | 8/2005 | Stöckl | |
| 6,926,525 B1 | 8/2005 | Ronvig | |
| 6,939,136 B2 | 9/2005 | Nielsen | |
| 6,939,489 B2 | 9/2005 | Moszner | |
| 6,942,699 B2 | 9/2005 | Stone | |
| 6,953,383 B2 | 10/2005 | Rothenberger | |
| 6,957,118 B2 | 10/2005 | Kopelman | |
| D511,833 S | 11/2005 | Wohrle | |
| 6,966,772 B2 | 11/2005 | Malin | |
| 6,970,760 B2 | 11/2005 | Wolf | |
| 6,971,877 B2 | 12/2005 | Harter | |
| 6,984,392 B2 | 1/2006 | Bechert et al. | |
| 6,994,549 B2 | 2/2006 | Brodkin | |
| 7,010,150 B1 | 3/2006 | Pfeiffer | |
| 7,010,153 B2 | 3/2006 | Zimmermann | |
| 7,012,988 B2 | 3/2006 | Adler | |
| 7,018,207 B2 | 3/2006 | Prestipino | |
| 7,021,934 B2 | 4/2006 | Aravena | |
| 7,029,275 B2 | 4/2006 | Rubbert | |
| 7,044,735 B2 | 5/2006 | Malin | |
| 7,056,115 B2 | 6/2006 | Phan | |
| 7,056,117 B2 | 6/2006 | Simmons, Jr. | |
| 7,056,472 B1 | 6/2006 | Behringer | |
| 7,059,856 B2 | 6/2006 | Marotta | |
| 7,066,736 B2 | 6/2006 | Kumar | |
| 7,067,169 B2 | 6/2006 | Liu et al. | |
| 7,084,868 B2 | 8/2006 | Farag | |
| 7,086,860 B2 | 8/2006 | Schuman | |
| 7,097,451 B2 | 8/2006 | Tang | |
| 7,104,795 B2 | 9/2006 | Dadi | |
| 7,110,844 B2 | 9/2006 | Kopelman | |
| 7,112,065 B2 | 9/2006 | Kopelman | |
| 7,118,375 B2 | 10/2006 | Durbin | |
| D532,991 S | 12/2006 | Gozzi | |
| 7,153,132 B2 | 12/2006 | Tedesco | |
| 7,153,135 B1 | 12/2006 | Thomas | |
| 7,163,443 B2 | 1/2007 | Basler | |
| 7,175,434 B2 | 2/2007 | Brajnovic | |
| 7,175,435 B2 | 2/2007 | Andersson | |
| 7,178,731 B2 | 2/2007 | Basler | |
| 7,201,576 B2 | 4/2007 | Tricca et al. | |
| 7,214,062 B2 | 5/2007 | Morgan | |
| 7,220,124 B2 | 5/2007 | Taub | |
| 7,228,191 B2 | 6/2007 | Hofmeister | |
| 7,236,842 B2 | 6/2007 | Kopelman | |
| 7,255,561 B2 | 8/2007 | Tricca et al. | |
| 7,281,927 B2 | 10/2007 | Marotta | |
| 7,286,954 B2 | 10/2007 | Kopelman | |
| 7,291,013 B2 * | 11/2007 | Aravena | A61C 8/0006 433/173 |
| 7,303,420 B2 | 12/2007 | Huch | |
| 7,314,375 B2 | 1/2008 | Gault | |
| 7,319,529 B2 | 1/2008 | Babayoff | |
| 7,322,746 B2 | 1/2008 | Beckhaus | |
| 7,322,824 B2 | 1/2008 | Schmitt | |
| 7,324,680 B2 | 1/2008 | Zimmermann | |
| 7,329,122 B1 | 2/2008 | Scott | |
| 7,333,874 B2 | 2/2008 | Taub | |
| 7,335,876 B2 | 2/2008 | Eiff | |
| D565,184 S | 3/2008 | Royzen | |
| 7,338,286 B2 | 3/2008 | Porter et al. | |
| 7,341,756 B2 | 3/2008 | Liu et al. | |
| 7,367,801 B2 | 5/2008 | Saliger | |
| 7,379,584 B2 | 5/2008 | Rubbert | |
| D571,471 S | 6/2008 | Stöckl | |
| 7,381,191 B2 | 6/2008 | Fallah | |
| 7,383,094 B2 | 6/2008 | Kopelman | |
| D575,747 S | 8/2008 | Abramovich | |
| 7,421,608 B2 | 9/2008 | Schron | |
| 7,425,131 B2 | 9/2008 | Amber | |
| 7,429,175 B2 | 9/2008 | Gittelson | |
| 7,435,088 B2 | 10/2008 | Brajnovic | |
| 7,476,100 B2 | 1/2009 | Kuo | |
| 7,481,647 B2 | 1/2009 | Sambu | |
| 7,484,959 B2 | 2/2009 | Porter et al. | |
| 7,488,174 B2 | 2/2009 | Kopelman | |
| 7,491,058 B2 | 2/2009 | Jorneus et al. | |
| 7,497,619 B2 | 3/2009 | Stoeckl | |
| 7,497,983 B2 | 3/2009 | Khan | |
| 7,520,747 B2 | 4/2009 | Stonisch | |
| 7,522,764 B2 | 4/2009 | Schwotzer | |
| 7,534,266 B2 | 5/2009 | Kluger | |
| 7,536,234 B2 | 5/2009 | Kopelman | |
| 7,545,372 B2 | 6/2009 | Kopelman | |
| 7,551,760 B2 | 6/2009 | Scharlack | |
| 7,555,403 B2 | 6/2009 | Kopelman | |
| 7,556,496 B2 | 7/2009 | Cinader, Jr. | |
| 7,559,692 B2 | 7/2009 | Beckhaus | |
| 7,563,397 B2 | 7/2009 | Schulman | |
| D597,769 S | 8/2009 | Richter | |
| 7,572,058 B2 | 8/2009 | Pruss | |
| 7,572,125 B2 | 8/2009 | Brajnovic | |
| 7,574,025 B2 | 8/2009 | Feldman | |
| 7,578,673 B2 | 8/2009 | Wen | |
| 7,580,502 B2 | 8/2009 | Dalpiaz | |
| 7,581,951 B2 | 9/2009 | Lehmann | |
| 7,582,855 B2 | 9/2009 | Pfeiffer | |
| 7,628,537 B2 | 12/2009 | Schulze-Ganzlin | |
| 7,632,097 B2 | 12/2009 | Clerck | |
| 7,653,455 B2 | 1/2010 | Cnader, Jr. | |
| 7,654,823 B2 | 2/2010 | Dadi | |
| 7,655,586 B1 | 2/2010 | Brodkin | |
| 7,658,610 B2 | 2/2010 | Knopp | |
| 7,661,956 B2 | 2/2010 | Powell | |
| 7,665,989 B2 | 2/2010 | Brajnovic | |
| 7,679,723 B2 | 3/2010 | Schwotzer | |
| 7,687,754 B2 | 3/2010 | Eiff | |
| 7,689,308 B2 | 3/2010 | Holzner | |
| D614,210 S | 4/2010 | Basler | |
| 7,698,014 B2 | 4/2010 | Dunne | |
| 7,708,559 B2 * | 5/2010 | Wohrle | A61C 8/0018 433/174 |
| 7,729,794 B2 | 6/2010 | Maier et al. | |
| 7,758,346 B1 | 7/2010 | Letcher | |
| 7,774,084 B2 | 8/2010 | Cinader, Jr. | |
| 7,780,446 B2 | 8/2010 | Sanchez et al. | |
| 7,780,907 B2 | 8/2010 | Schmidt | |
| 7,785,007 B2 | 8/2010 | Stoeckl | |
| 7,787,132 B2 | 8/2010 | Körner | |
| 7,796,811 B2 | 9/2010 | Orth | |
| 7,798,708 B2 | 9/2010 | Erhardt | |
| 7,801,632 B2 | 9/2010 | Orth | |
| 7,815,371 B2 | 10/2010 | Schulze-Ganzlin | |
| 7,824,181 B2 | 11/2010 | Sers | |
| D629,908 S | 12/2010 | Jerger | |
| 7,855,354 B2 | 12/2010 | Eiff | |
| 7,865,261 B2 | 1/2011 | Pfeiffer | |
| 7,876,877 B2 | 1/2011 | Stockl | |
| 7,901,209 B2 | 3/2011 | Saliger | |
| 7,906,132 B2 | 3/2011 | Ziegler et al. | |
| 7,982,731 B2 | 7/2011 | Orth | |
| 7,985,119 B2 | 7/2011 | Basler | |
| 7,986,415 B2 | 7/2011 | Thiel | |
| 7,988,449 B2 | 8/2011 | Amber | |
| 8,011,925 B2 | 9/2011 | Powell | |
| 8,011,927 B2 | 9/2011 | Merckmans, III | |
| 8,026,943 B2 | 9/2011 | Weber | |
| 8,033,826 B2 | 10/2011 | Towse et al. | |
| 8,038,440 B2 | 10/2011 | Swaelens | |
| 8,043,091 B2 | 10/2011 | Schmitt | |
| 8,047,895 B2 | 11/2011 | Basler | |
| 8,057,912 B2 | 11/2011 | Basler | |
| 8,062,034 B2 | 11/2011 | Hanisch | |
| 8,070,485 B2 | 12/2011 | Schwartz et al. | |
| 8,075,313 B2 | 12/2011 | Ranck | |
| 8,083,522 B2 | 12/2011 | Karkar | |
| 8,105,081 B2 | 1/2012 | Bazar | |
| 8,177,557 B2 | 5/2012 | Delmonico et al. | |
| 8,185,224 B2 | 5/2012 | Powell et al. | |

(56) References Cited

U.S. PATENT DOCUMENTS

| | | |
|---|---|---|
| 8,226,654 B2 | 7/2012 | Ranck |
| 8,257,083 B2 | 9/2012 | Berckmans, III et al. |
| 8,272,870 B2 | 9/2012 | Van Lierde |
| 8,292,621 B2 * | 10/2012 | Laizure, Jr. ............ A61C 8/008 433/172 |
| 8,309,162 B2 | 11/2012 | Charlton et al. |
| 8,382,477 B2 * | 2/2013 | Philibin ................ A61C 8/008 433/173 |
| 8,401,826 B2 | 3/2013 | Cheng et al. |
| 8,425,231 B1 | 4/2013 | Hochman et al. |
| D692,561 S | 10/2013 | Hochman et al. |
| 8,602,783 B2 | 12/2013 | Fudim |
| 8,777,611 B2 | 7/2014 | Cios |
| D713,964 S | 9/2014 | Hochman et al. |
| 9,089,382 B2 | 7/2015 | Hochman |
| 2001/0008751 A1 | 7/2001 | Chishti |
| 2001/0034010 A1 | 10/2001 | MacDougald |
| 2002/0010568 A1 | 1/2002 | Rubbert |
| 2002/0028418 A1 | 3/2002 | Farag |
| 2002/0039717 A1 | 4/2002 | Amber |
| 2002/0160337 A1 | 10/2002 | Klein |
| 2002/0167100 A1 | 11/2002 | Moszner |
| 2003/0130605 A1 | 7/2003 | Besek |
| 2003/0222366 A1 | 12/2003 | Stangel |
| 2004/0029074 A1 | 2/2004 | Brajnovic |
| 2004/0048227 A1 | 3/2004 | Brajnovic |
| 2004/0121286 A1 | 6/2004 | Aravena et al. |
| 2004/0132603 A1 | 7/2004 | Narhi et al. |
| 2004/0180308 A1 | 9/2004 | Ebi |
| 2004/0219477 A1 | 11/2004 | Harter |
| 2004/0219479 A1 | 11/2004 | Malin |
| 2004/0219490 A1 | 11/2004 | Gartner |
| 2004/0220691 A1 | 11/2004 | Hofmeister |
| 2004/0241611 A1 | 12/2004 | Amber |
| 2004/0243481 A1 | 12/2004 | Bradbury |
| 2004/0259051 A1 | 12/2004 | Brajnovic |
| 2005/0023710 A1 | 2/2005 | Brodkin |
| 2005/0056350 A1 | 3/2005 | Dolabdjian |
| 2005/0070782 A1 | 3/2005 | Brodkin |
| 2005/0084144 A1 | 4/2005 | Feldman |
| 2005/0084821 A1 * | 4/2005 | Sims ...................... A61C 8/005 433/173 |
| 2005/0100861 A1 | 5/2005 | Choi |
| 2005/0170311 A1 | 8/2005 | Tardieu |
| 2005/0271996 A1 | 12/2005 | Sporbert |
| 2005/0277089 A1 | 12/2005 | Brajnovic |
| 2005/0277090 A1 | 12/2005 | Anderson |
| 2005/0277091 A1 | 12/2005 | Andersson |
| 2005/0282106 A1 | 12/2005 | Sussman |
| 2005/0283065 A1 | 12/2005 | Babayoff |
| 2006/0006561 A1 | 1/2006 | Brajnovic |
| 2006/0008763 A1 | 1/2006 | Brajnovic |
| 2006/0008770 A1 | 1/2006 | Brajnovic |
| 2006/0046229 A1 | 3/2006 | Teich |
| 2006/0064758 A1 | 3/2006 | Petner et al. |
| 2006/0093988 A1 | 5/2006 | Swaelens |
| 2006/0094951 A1 | 5/2006 | Dean |
| 2006/0127848 A1 | 6/2006 | Sogo |
| 2006/0210949 A1 | 9/2006 | Stoop |
| 2006/0240385 A1 | 10/2006 | Gatti |
| 2006/0252009 A1 | 11/2006 | Gogarnoiu |
| 2006/0263741 A1 | 11/2006 | Imgrund |
| 2006/0281041 A1 | 12/2006 | Rubbert |
| 2007/0015111 A1 | 1/2007 | Kopelman |
| 2007/0031790 A1 | 2/2007 | Raby |
| 2007/0065777 A1 | 3/2007 | Becker |
| 2007/0077532 A1 | 4/2007 | Harter |
| 2007/0092854 A1 | 4/2007 | Powell |
| 2007/0141525 A1 | 6/2007 | Cinader, Jr. |
| 2007/0160954 A1 | 7/2007 | Steiner |
| 2007/0202462 A1 * | 8/2007 | Schwarz .............. A61C 8/0012 433/172 |
| 2007/0211081 A1 | 9/2007 | Quadling |
| 2007/0218426 A1 | 9/2007 | Quadling |
| 2007/0264612 A1 | 11/2007 | Mount |
| 2007/0269769 A1 | 11/2007 | Marchesi |
| 2007/0281277 A1 | 12/2007 | Brajnovic |
| 2008/0038692 A1 | 2/2008 | Andersson |
| 2008/0044794 A1 | 2/2008 | Brajnovic |
| 2008/0057467 A1 | 3/2008 | Gittelson |
| 2008/0070181 A1 | 3/2008 | Abolfathi |
| 2008/0085489 A1 | 4/2008 | Schmitt |
| 2008/0090210 A1 | 4/2008 | Brajnovic |
| 2008/0114371 A1 | 5/2008 | Kluger |
| 2008/0118895 A1 | 5/2008 | Brajnovic |
| 2008/0124676 A1 | 5/2008 | Marotta |
| 2008/0153060 A1 | 6/2008 | De Moyer |
| 2008/0153061 A1 | 6/2008 | Marcello |
| 2008/0153065 A1 | 6/2008 | Brajnovic |
| 2008/0153069 A1 | 6/2008 | Holzner |
| 2008/0176189 A1 | 7/2008 | Stonisch |
| 2008/0206714 A1 | 8/2008 | Schmitt |
| 2008/0233537 A1 | 9/2008 | Amber |
| 2008/0233539 A1 | 9/2008 | Rossler |
| 2008/0241798 A1 | 10/2008 | Holzner |
| 2008/0261165 A1 | 10/2008 | Steingart |
| 2008/0261176 A1 | 10/2008 | Hurson |
| 2008/0286722 A1 | 11/2008 | Berckmans, III |
| 2008/0300716 A1 | 12/2008 | Kopelman |
| 2009/0017418 A1 | 1/2009 | Gittelson |
| 2009/0026643 A1 | 1/2009 | Wiest |
| 2009/0042167 A1 | 2/2009 | Van Der Zel |
| 2009/0047629 A1 * | 2/2009 | Kim ...................... A61C 8/005 433/173 |
| 2009/0081616 A1 | 3/2009 | Pfeiffer |
| 2009/0087817 A1 | 4/2009 | Jansen |
| 2009/0092948 A1 | 4/2009 | Gantes |
| 2009/0098510 A1 | 4/2009 | Zhang |
| 2009/0098511 A1 | 4/2009 | Zhang |
| 2009/0123045 A1 | 5/2009 | Quadling |
| 2009/0123887 A1 | 5/2009 | Brajnovic |
| 2009/0130630 A1 | 5/2009 | Suttin |
| 2009/0186319 A1 | 7/2009 | Sager |
| 2009/0187393 A1 | 7/2009 | Van Lierde |
| 2009/0220134 A1 | 9/2009 | Cahill |
| 2009/0220916 A1 | 9/2009 | Fisker |
| 2009/0220917 A1 | 9/2009 | Jensen |
| 2009/0239195 A1 | 9/2009 | Wohrle et al. |
| 2009/0239197 A1 | 9/2009 | Brajnovic |
| 2009/0239200 A1 | 9/2009 | Brajnovic |
| 2009/0253097 A1 | 10/2009 | Brajnovic |
| 2009/0263764 A1 | 10/2009 | Berckmans, III |
| 2009/0287332 A1 | 11/2009 | Adusumilli |
| 2009/0298009 A1 | 12/2009 | Brajnovic |
| 2009/0298017 A1 | 12/2009 | Boerjes |
| 2009/0317763 A1 | 12/2009 | Brajnovic |
| 2009/0325122 A1 | 12/2009 | Brajnovic |
| 2010/0009314 A1 | 1/2010 | Tardieu |
| 2010/0028827 A1 | 2/2010 | Andersson |
| 2010/0038807 A1 | 2/2010 | Brodkin |
| 2010/0075275 A1 | 3/2010 | Brajnovic |
| 2010/0092904 A1 | 4/2010 | Esposti |
| 2010/0105008 A1 | 4/2010 | Powell |
| 2010/0151420 A1 | 6/2010 | Ranck |
| 2010/0151423 A1 | 6/2010 | Ranck |
| 2010/0173260 A1 | 7/2010 | Sogo |
| 2010/0209877 A1 | 8/2010 | Hogan |
| 2010/0280798 A1 | 11/2010 | Pattijn |
| 2010/0330533 A1 | 12/2010 | Cottrell |
| 2011/0008751 A1 | 1/2011 | Pettersson |
| 2011/0027339 A1 | 2/2011 | Mao |
| 2011/0060558 A1 | 3/2011 | Pettersson |
| 2011/0123959 A1 | 5/2011 | Sicurelli |
| 2011/0129792 A1 | 6/2011 | Berckmans, III |
| 2011/0159455 A1 | 6/2011 | Stumpel |
| 2011/0183289 A1 | 7/2011 | Powell |
| 2011/0191081 A1 | 8/2011 | Malfliet |
| 2011/0200967 A1 | 8/2011 | Laizure, Jr. |
| 2011/0244426 A1 | 10/2011 | Amber |
| 2011/0269104 A1 | 11/2011 | Berckmans, III |
| 2011/0275032 A1 | 11/2011 | Tardieu |
| 2011/0306008 A1 | 12/2011 | Suttin |
| 2011/0306009 A1 | 12/2011 | Suttin |
| 2011/0306014 A1 | 12/2011 | Conte |

(56) References Cited

U.S. PATENT DOCUMENTS

| | | | |
|---|---|---|---|
| 2012/0010740 A1 | 1/2012 | Swaelens | |
| 2012/0135370 A1 | 5/2012 | Ranck | |
| 2012/0164593 A1 | 6/2012 | Bavar | |
| 2012/0164893 A1 | 6/2012 | Misuzuka | |
| 2012/0214130 A1 | 8/2012 | Krivoruk | |
| 2012/0264081 A1* | 10/2012 | Philibin | A61C 8/008 433/173 |
| 2012/0282573 A1 | 11/2012 | Mao | |
| 2013/0101964 A1 | 4/2013 | Fudim | |
| 2013/0288200 A1 | 10/2013 | Battula | |
| 2013/0288202 A1 | 10/2013 | Hochman et al. | |
| 2014/0205969 A1* | 7/2014 | Marlin | A61C 8/0001 433/173 |
| 2015/0004563 A1* | 1/2015 | Blaisdell | A61C 13/34 433/173 |
| 2015/0056573 A1 | 2/2015 | Collins et al. | |
| 2015/0289952 A1 | 10/2015 | Hochman et al. | |

FOREIGN PATENT DOCUMENTS

| | | |
|---|---|---|
| GB | 1 304 612 A | 1/1973 |
| JP | 2008531095 | 8/2008 |
| WO | WO 1994/26200 | 11/1994 |
| WO | WO 1999/032045 | 7/1999 |
| WO | WO 2000/008415 | 2/2000 |
| WO | WO 2001/058379 | 8/2001 |
| WO | WO 2002/053055 | 7/2002 |
| WO | WO 2003/024352 | 3/2003 |
| WO | WO 2004/030565 | 4/2004 |
| WO | WO 2004/037110 | 5/2004 |
| WO | WO 2004/075771 | 9/2004 |
| WO | WO 2004/087000 | 10/2004 |
| WO | WO 2004/098435 | 11/2004 |
| WO | WO 2006/014130 | 2/2006 |
| WO | WO 2006/062459 | 6/2006 |
| WO | WO 2006/082198 | 8/2006 |
| WO | WO 2007/005490 | 1/2007 |
| WO | WO 2007/033157 | 3/2007 |
| WO | WO 2007/104842 | 9/2007 |
| WO | WO 2007/129955 | 11/2007 |
| WO | WO 2008/057955 | 5/2008 |
| WO | WO 2008/083857 | 7/2008 |
| WO | WO 2009/146164 | 12/2009 |

OTHER PUBLICATIONS

BIOMET 3i—Manual entitled "Navigator™ System for CT Guided Surgery Manual", Revision A Oct. 2007—34 pages.
Goulette, Francois. "A New Method and a Clinical case for Computer Assisted Dental Implantology." Retrieved from Summer European university in surgical Robotics, URL:www.lirmm.fr/manifs/UEE/docs/students/goulette.pdf, Sep. 6, 2003 (7 pages).
Jakob Brief, "Accuracy of image-guided implantology." Retrieved from Google, <URL:sitemaker.umich.edu/sarmentlab/files/robodent_vs_denx_coir_05.pdf, Aug. 20, 2004 (7 pages).
Machine Design: "Robots are ready for medical manufacturing." Retrieved from MachineDesign.Com, <URL: http://machinedesign.com/article/robots-are-ready-for-medical-manufacturing-0712>, Jul. 12, 2007 (7 pages).
MedNEWS: "'Surgical Glue' May Help to Eliminate Suturing for Implants." Retrieved from MediNEWS.Direct, URL:http://www.medinewsdirect.com/?p=377, Dec. 21, 2007 (1 page).
European Application Serial No. 12866657.5, Extended European Search Report dated Sep. 14, 2015 (8 pages).
International Application Serial No. PCT/US2012/068078, International Search Report dated Feb. 15, 2013 (3 pages).
International Application Serial No. PCT/US2012/068078, Written Opinion dated Feb. 15, 2013 (5 pages).
Becker, C. et al. "Current theories of crown contour, margin placement, and pontic design"; J. Prosth. Dent.; Feb. 2005; pp. 107-115 (9 pages).
Frojd, Victoria, et al. "Effect of Nanoporous Ti02 Coating and Anodized Ca2 Modification of Titanium Surfaces on Early Microbial Biofilm Formation"; BMC Oral Health, 2011 (9 pages).
Nevins, M. et al. "Histologic Evidence of a Connective Tissue Attachment to Laser Microgrooved Abutments: A Canine Study"; The Intl. J. Perio. & Rest. Dentistry, vol. 30, No. 3, 2010 (12 pages).
Rossi, S. et al. "Peri-implant tissue response to Ti02 surface modified implants"; Clin. Oral Impl. Res. 19, pp. 348-355; 2009 (8 pages).
Biomet 3i et al. "Immediate Provisional Restoration of Implants with PreFormance Provisional Components"; PreFormance Temporary Cylinder Brochure; 2007 (6 pages).
Biomet 3i; "NanoTite Prevail Implants: Crestal Bone Preservation in Aesthetic Zone"; ARTIOI IA NanoTite Implant System Brochure, vol. 6, Issue 2; 2007 (1 page).
Biomet 3i; "Osseotite Implants, Restorative Manual"; 2009 (116 pages).
Biomet 3i et al. "Provisionalization with Soft Tissue Sculpting Prior to Fabrication of a CAD/CAM Abutment"; ART1060 EncodeCP Brochure, vol. 7, Issue 3; 2009 (8 pages).
Biomet 3i; "Rapid Adjustment, Enduring Strength Aesthetic Design"; ART953C PreFormance Brochure; 2008 (4 pages).
"Restoration of Immediate Temporary Crown Cases: Guidance"; OsseoNews; [Online] retrieved from the internet: http://www.osseonews.com/restoration-of-immediate-temporary-crown-cases-guidance/; Mar. 20, 2009 (6 pages).
Biomet 3i; "Your Patients Require Immediate Aesthetic Solutions—Biomet 3i Has Optimal Products"; ARTI 018 Provisional Components Brochure; 2009 (5 pages).
Giordano, R. "Zirconia: A Proven, Durable Ceramic for Esthetic Restorations"; Compendium, Clin. Materials Rev., vol. 33, No. 1; 2012 (4 pages).
Kan, J. et al. "Immediate Placement and Provisionalization of Maxillary Anterior Single Implants: A Surgical and Prosth. Rationale"; Pract. Periodont. Aesthet. Dent., pp. 817-824; 2000 (8 pages).
Kan, J. et al. "Interimplant Papilla Preservation in the Esthetic Zone: A Report of Six Consecutive Cases"; Intl. J. Perio. & Rest. Dentistry, vol. 23, No. 3; 2003 (12 pages).
Perry, R. et al. "Provisional Materials: Key Components of Interim Fixed Restorations"; 2012 (3 pages).
Wohrle, S. "Single-Tooth Replacement in the Aesthetic Zone with Immediate Provisionalization: Fourteen Consecutive Case Reports"; Pract. Periodont. Aesthet. Dent., pp. 1107-1114; 1998 (8 pages).
Areva, S. et al. "Use of sol-gel-derived titania coating for direct soft tissue attachment"; Wiley Periodicals, Inc., Turku, Finland; Jun. 2, 2004.
Kim, T H. et al. "Simulated Tissue Using a Unique Pontic Design: A Clinical Report"; J. Prosth. Dent.; vol. 102, No. 4; pp. 205-210 (6 pages).
Tinker, ET. "Sanitary dummies." Dental Review 1918; 32:401-408.
Goldstein, G. et al. "Finding Z: A Mathematical Method for Predicting Tissue Position After Implant Abutment-Restoration Placement"; J. Prosth. Dent., Aug. 2014, vol. 112, Issue 2; pp. 322-324 (3 pages).
Irving, A.J. "A consideration of modern methods for supplying missing teeth with fixed bridgework." Dent Cosmos 1928;70: 191-8.
Dewey, K.W. et al. "An experimental study of tissue reaction about porcelain roots." J. Dent. Res. 1933; 13:459-472.
Stein, R.S. "Pontic-residual ridge relationship: a research report." J. Prosth. Dent. 1966; 16:251-85.
Banerjee, R. et al. "Ovate Pontic Design: An Aesthetic Solution to Anterior Missing Tooth—A Case Report"; J. Clin. & Diag. Res. [serial online], Aug. 2010 [cited Aug. 31, 2010]; 4:2996-2999; http://www.jcdr.net/back_issues.asp?issn=0973-709x&year=2010&month=Aug&volume=4&issue=3&page=2996-2999&id=604 (5 pages).
Garber, D.A. et al. "The edentulous ridge in fixed prosthodontics." Compend. Contin. Educ. Dent. 1981; 2: 212-23.
Miller, M.B. "Aesthetic anterior reconstruction using a combined periodontal /restorative approach." Pract Periodontics Aesthet. Dent. 1993; 5:33-40.

(56) References Cited

OTHER PUBLICATIONS

Dylina, T.J. "Contour determination for ovate pontics." J. Prosth. Dent. 1999; 82: 136-142.
Thoma, et al. "Soft Tissue Volume Augmentation by the use of Collagen-based Matrices: a volumetric analysis." J. Clin. Periodontal, 2010; 37:659-666.
Trimpou, G. et al. "Rationale for esthetic tissue preservation of a fresh extraction socket by an implant treatment concept simulating a tooth replantation." Dent. Traumatol. 2010; 26(1):105-111.
Zitzmann, N., DMD, et al. "The Ovate pontic design: A histologic observation in humans"; J. Prosth. Dent., Oct. 2002, vol. 88, No. 4:375-380.
Orsini, G., DDS, MSc, PhD, et al. "Tissue healing under provisional restorations with ovate pontics: A pilot human histological study"; J. Prosth. Dent., Oct. 2006, vol. 96, No. 4:252-257.
Dylina, T.J. "Contour determination for ovate pontics." J. Prosth. Dent. 1999, vol. 82, No. 2: 136-142.
Jacques, L.B. et al. "Tissue sculpturing: An alternative method for improving esthetics of anterior fixed prosthodontics." J. Prosth. Dent. 1999; 81(5):630-633.
Schlee, M. Aesthetic and patient preference using a bone substitute to preserve extraction sockets under pontics. A cross-sectional survey. Eur J Oral Implantol 2009, 2(3): 209-217.
Tan-Chu, J., DDS, et al. "Analysis of Buccolingual Dimensional Changes of the Extraction Socket Using the 'Ice Cream Cone' Flapless Grafting Technique"; Intl. J. Periodont. & Rest. Dent. 2014; vol. 34, No. 3:399-403.
Fickl, S. et al, "Dimensional changes of the alveolar ridge contour after different socket preservation techniques"; J. Clin. Periodont. 2008; 35:906-913.
Araujo, M.G. et al. "Dynamics of Bio-Oss Collagen incorporation in fresh extraction wounds: an experimental study in the dog"; Clin. Oral Impl. Res. 21, 2010:55-64.
Araujo, M.G. et al. "Ridge preservation with the use of Bio-Oss collagen: A 6 month study in the dog"; Clin. Oral Impl. Res. 20, 2009:433-440.
Araujo, M.G. et al. "Dimensional ridge alterations following tooth extraction. An experimental study in the dog"; J. Clin. Periodont. 2005; 32:212-218.
Araujo, M.G. et al. "Ridge alterations following implant placement in fresh extraction sockets: an experimental study in the dog"; J. Clin. Periodont. 2005; 32:645-652 doi: 10.1111/j.1600-051X.2005.00726.x (8 pages).
Schropp, L. et al. "Bone healing and soft tissue contour changes following single-tooth extraction: a clinical and radiographic 12-month prospective study." Intl. J. Periodont. Rest. Dent. 2003; 23(4):313-323.
Waerhaug, J. et al. "Implantation of acrylic roots in tooth sockets." Oral Surg. Oral Med. Oral Pathol. 1956; 9(1):46-54.
Waerhaug, J. et al. "Reaction of gingival tissues to self-curing acrylic restorations." J. Am. Dent. Assoc. 1957; 54(6):760-768.
Waerhaug, J. "Tissue reaction around acrylic root tips." J. Dent. Res. 1957; 36(1):27-38.
Waerhaug, J. Ph.D. "Tissue Reactions Around Artificial Crowns"; Inst. Dent. Res., Josefinegaten 32; J. Periodont.; pp. 172-185 (14 pages).
Loe, H. et al. "Experimental replantation of teeth in dogs and monkeys." Arch Oral Biology 1961; 3:176-184.
Hodosh, M. et al. "Implants of acrylic teeth in human beings and experimental animals; Clinical and microscopic studies." Oral Surg. Oral Med. Oral Pathol. 1964; 18:569-579.
Hodosh, M. et al. "The dental polymer implant concept." J. Prosthet. Dent. 1969; 22(3):371-380.
Schropp et al. "Bone Healing Following Immediate Versus Delayed Placement of Titanium Implants into Extraction Sockets: A Prospective Clinical Study." Intl. J. Oral & Maxillofacial Implants, vol. 18, No. 2, pp. 189-199 (2003) (12 pages).
Kim, T. H. et al. "Restoration Using Gingiva-Colored Ceramic and a Ridge Lap Pontic With Circumferential Pressure: A Clinical Report"; J. Prosth. Dent., 2010, vol. 104, Issue 2, pp. 71-76.
Gahan, M. et al. "The Ovate Pontic for Fixed Bridgework"; Dental Update, Jul./Aug. 2012, pp. 407-415.
Becker, W. "Immediate implant placement: treatment planning and surgical steps for successful outcomes"; British Dental Journal, Aug. 26, 2006; vol. 201, No. 4, pp. 199-205.
Coachman, C. et al. "Prosthetic Gingival Reconstruction in Fixed Partial Restorations. Part 3: Laboratory Procedures and Maintenance"; Intl. J. Periodont. & Restorative Dent.; Quintessence Publishing Co., Inc.; 2010; vol. 30, No. 1, pp. 19-29.
Edelhoff, D. et al. "HIP zirconia fixed partial dentures—Clinical results after 3 years of clinical service"; Quintessence International, Quintessence Publishing Co., Inc.; 2008; vol. 39, No. 6, pp. 459-471.
Caplanis, N. et al. "Extraction Defect Assessment, Classification, and Management"; CDA Journal, The EDS Classification, Nov. 2005, vol. 33, No. 11, pp. 853-863.
Schlee, M. et al. "Aesthetic and patient reference using a bone substitute to preserve extraction sockets under pontics. A cross-sectional survey"; Eur. J. Oral Implantol., 2009, pp. 209-217.
Chee, W. "Provisional restorations in soft tissue management"; Periodontology 2000, vol. 27, 2001, pp. 139-147.
Becker, W. et al. "Immediate implant placement: treatment planning and surgical steps for successful outcome"; Periodontology 2000, vol. 47, 2008, pp. 79-89.
Liu, C.-L. "Use of a Modified Ovate Pontic in Areas of Ridge Defects: A Report of Two Cases"; J. Esthetic & Restor. Dent., 2004, vol. 16, No. 5, pp. 273-283.
Priest, G. "Esthetic Potential of Single-Implant Provisional Restorations: Selection Criteria of Available Alternatives"; J. Esthetic & Restor. Dent., 2006, vol. 18, No. 6, pp. 326-339.
Tischler, M. "Dental Implants in the Esthetic Zone"; NYSDJ, Mar. 2004, pp. 22-26.
Kois, J. "Predictable Peri-Implant Gingival Aesthetics: Surgical and Prosthodontic Rationales"; Prat. Proced. Aesthet. Dent., 2001, vol. 13, No. 9, pp. 691-698.
Kan, J. et al. "Computer-Guided Immediate Provisionalization of Anterior Multiple Adjacent Implants: Surgical and Prosthodontic Rationale"; Pract. Proced. Aesthet. Dent., 2006, vol. 18, No. 10, pp. A-G.
Levine, R. "Soft Tissue Considerations for Optimizing Implant Esthetics"; Functional Esthetics & Restorative Dentistry, Series 1, No. 2, pp. 54-62.
Armin, R. "The Ovate Pontic-Ramsey Amin DDS of Burbank Explains This Dental Implant Bridge Detail"; http://www.burbankdentalimplants.com/the-ovate-pontic-ramsey-amin- . . . ; Feb. 10, 2015 (5 pages).
Supplementary European Search Report from Application No. EP 16 76 2350 dated Nov. 15, 2018.

\* cited by examiner

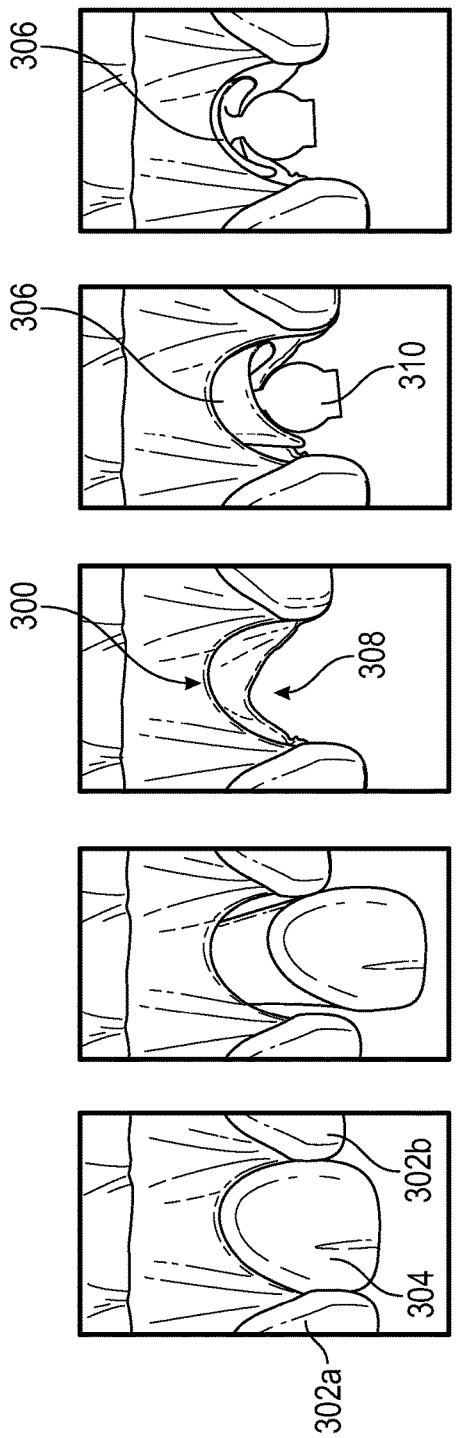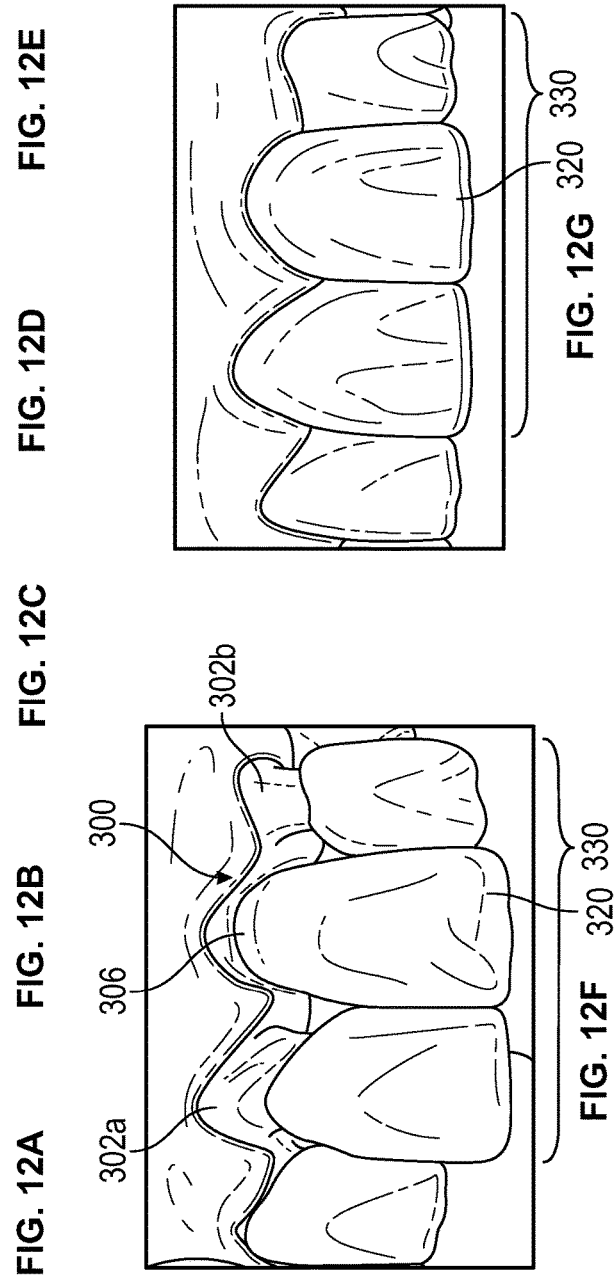

GINGIVAL OVATE PONTIC AND METHODS OF USING THE SAME

CROSS-REFERENCE TO RELATED APPLICATION

This application claims the benefit of U.S. Provisional Patent Application No. 62/130,074, filed Mar. 9, 2015, which is hereby incorporated herein by reference in its entirety.

FIELD OF THE INVENTION

The present invention relates generally to the field of prosthetic and restorative dentistry and, in particular, to a gingival ovate pontic device and methods of using the same to maintain hard and soft tissue architecture of a tooth-extraction site.

BACKGROUND OF THE INVENTION

The tooth is a vital structure of the oral cavity that is responsible for chewing (masticating) food and for providing a pleasing aesthetic appearance. Anatomically, teeth reside within the oral cavity, firmly anchored in the upper jaw (maxilla) or the lower jaw (mandible) within two distinct anatomic regions of the jaws and periodontium or supporting structures. The first anatomic region is the apical inferior portion of the tooth or root, which is connected to the jawbone via an attachment called the periodontal ligament. The portion of the jawbone that is connected to the tooth may be referred to as the bone or hard tissue zone. The second anatomic region is the superior portion of the tooth, called the anatomic or clinical crown, which is superior to the crest of the bone, including the visible portion of the tooth above the gingival line. The anatomic or clinical crown is connected to the jaw in the soft tissue or gingival region of the jawbone referred to as the soft tissue zone. The soft tissue zone forms a soft tissue collar around the neck of the tooth. The gingival surface that surrounds each tooth includes peaks (papillae) and valleys. The soft tissue-tooth attachment is composed of gingival fibers that insert into the superior aspect of the root surface to form the junctional epithelial and connective tissue (sulcular epithelium) attachments and, more specifically, the hemidesmosmal cell attachment to the root and crown surfaces.

The attachment of the gingival soft tissue to the tooth forms a biological adherence or seal between the gingival tissues and the surface of the tooth. This biological seal plays an important role in maintaining the health of the oral cavity by inhibiting or preventing the ingress of oral bacteria and foreign substances through the soft tissue zone/tooth interface to the underlying bone.

The inability to reestablish the biologic seal after the removal of a tooth has many repercussions to bone and soft tissue regeneration and on soft tissue changes to both the macro- and micro-anatomy of the gingiva. For example, the soft tissue zone plays an essential role in maintaining and preserving dental aesthetics. The spatial relationship of the teeth, the color of the teeth, and the soft tissue gingival architecture are important factors in maintaining desirable dental aesthetics. The loss or alteration of any of these factors generally leads to an inferior aesthetic outcome and/or a potential risk of disease for the patient.

In an era of dentistry driven by high aesthetic demands and standards, post-extraction tissue loss can pose a considerable aesthetic, surgical, and/or restorative challenge. For example, the loss of gingival attachment within the soft tissue zone may lead to the irreversible loss of the interdental papillae and the gingival architecture surrounding a prosthetic tooth or dental restoration. In vivo studies report up to about 3-6 mm of bucco-lingual volumetric remodeling within the first six months following extraction of non-molar teeth. This dimensional change is attributed to soft tissue collapse in the edentulous space immediately following tooth extraction, which can significantly alter the midfacial gingival architecture and/or create an aesthetically displeasing "shadowing" effect around the final restoration. There are currently no predictable surgical techniques available to correct the gingival changes to vertical height and horizontal dimensions of the interdental papillae after tooth removal.

As such, it is critical to consider proper tissue (e.g., periodontal tissue) management during the treatment planning phase to achieve consistent treatment outcomes and, specifically, to maintain pre-extraction gingival morphology and architecture of the edentulous ridge. This concept is often referred to as guided soft tissue preservation.

Several procedures have been proposed to assist in addressing the disadvantages associated with post-extraction tissue loss. Surgical interventions include extraction socket preservation techniques, immediate implant placement, and alveolar bone grafting, which are used to minimize significant post-extraction hard and soft tissue dimensional changes. However, immediate implant placement and bone grafting may not be viable treatment options in certain clinical situations such as inadequate buccal plate volume post-extraction, patients with medical limitations, limited time, and/or limited finances, or the like. Furthermore, existing devices and methods have been generally unsuccessful in providing a minimally invasive technique to reestablish a biologic seal surrounding a tooth-extraction site after tooth removal.

For example, barrier membranes for guided tissue bone regeneration (GTR) have been used to assist in maintaining, preserving, and/or regenerating lost bone after, e.g., periodontal disease. Barrier membranes generally assist in creating a protective barricade by inhibiting or preventing the migration of unwanted cells (e.g., connective tissue cells) to the post-extraction socket such that the post-extraction socket can be refilled with bone cells (e.g., osteoblasts) known to assist with bone growth.

One disadvantage associated with using barrier membranes is the direct exposure of the barrier membrane to the oral environment, which may be due to the lack of an effective soft tissue zone-tooth seal. Additionally, once the membrane has been exposed to the oral environment, bacteria may colonize on the surface of the membrane, thereby potentially leading to infection and/or causing the bone to fail to regenerate. Such exposure may also lead to plaque accumulation on the surface of the membrane that is difficult, if not impossible, to clean/remove.

Collagen-type membranes may be less prone to plaque accumulation, but they may be more susceptible to dissolution (dissolving) once exposed to salivary enzymes, which may break down the collagen matrix after only a few days or weeks of exposure.

Some existing periodontal bone regeneration methods include inserting hard-tissue graft material (e.g., bone replacement substances) into the post-extraction socket. Non-limiting examples of bone replacement substances include autografts, allografts, xenografts, alloplastic grafts, and/or a variety of bone replacement and cell stimulating materials that may include bone morphogenic proteins (BMPs), stem cell derivatives, platelet rich proteins (PRPs)

derived from a patient's blood, and/or other biologic sources. One disadvantage associated with using bone replacement substances is the inability to contain and protect the substances from exposure to foreign substances during the critical healing phase due to an ineffective soft tissue zone-tooth biologic seal after tooth removal.

Another problem that often occurs after tooth extraction is the anatomic and physical collapse of the extraction socket and ridge. This collapse may occur with or without elevation of a mucoperiosteal flap. In some instances, ridge collapses ranging from about 2.2 mm (e.g., in cases where the flap was not elevated) to about 5.9 mm (e.g., in cases where the flap was elevated) have been reported. The use of a hard-tissue (e.g., bone) graft material placed in the extraction socket after tooth removal has been shown to be useful in reducing ridge collapse, but it is not without disadvantages. For example, bone grafts placed in extraction sockets often prematurely absorb, depending upon the type of graft used.

It is generally difficult to properly adapt the gingival or gum side of a temporary pontic restoration (e.g., coronal pontic portion) as part of a fixed dental prosthesis (FDP), whether tooth-borne or implant-borne. One obstacle is due to the fact that, after tooth removal, there is often a significant amount of localized bleeding into the extraction socket. The resultant formation, which may be described as a "liver" blood clot, may become a physical barrier, blocking provisional pontic restoration material from being properly adapted to the undersurface of the FDP. As such, the undersurface of the temporary pontic restoration area may not accurately mimic and represent the extraction socket site. Consequently, the undersurface of the temporary pontic restoration is often formed freehand by "eyeballing" the extracted socket site, which may or may not accurately represent the site. However, if properly formed, the undersurface of the temporary pontic restoration can physically support the mucosal soft tissues, thereby generally maintaining the shape of the extraction socket.

Pontics are advantageous because they emerge from the gingival tissues and generally mimic the cosmetic appearance of a natural tooth. Therefore, it is important to generally maintain the socket anatomy with the associated hard and soft tissues after tooth extraction to preserve the aesthetic appearance of the mucosal gingival tissues and their relationship to the pontic.

The devices and methods described herein assist in generally reestablishing the important biologic seal after tooth removal and in preserving the aesthetic and anatomic architecture of the tissue zone.

SUMMARY OF THE INVENTION

In one embodiment described herein, a pontic device for preserving soft tissue in a tooth-extraction site includes a generally curved apical end. The apical end has a first perimeter and is configured to rest in a tooth extraction socket and substantially conform to soft tissue of a tooth-extraction site immediately after a tooth has been extracted. The pontic device further includes an opposing, generally concave coronal end. The coronal end has a second perimeter that is configured to substantially correspond to and form a seal with gingival tissue surrounding the tooth-extraction site. The coronal end is configured to receive a tooth-shaped coronal pontic portion to form a final restoration.

In another embodiment described herein, a dental restoration method includes extracting a tooth from a tooth-extraction site. The tooth-extraction site has gingival tissue surrounding the tooth. The extracting results in an extraction socket having soft and hard tissue positioned therein. The method further includes selecting a gingival pontic device having an apical end substantially conforming to a shape of the extraction socket following the extraction and a coronal end having a perimeter substantially conforming to the gingival tissue surrounding the tooth-extraction site immediately following the extraction. The method further includes applying the gingival ovate pontic device to the extraction socket. The gingival ovate pontic device assists in substantially maintaining the shape of the soft tissue within the extraction socket during healing.

In another embodiment described herein, a kit of components for preservation of a tooth-extraction site includes a plurality of gingival ovate pontic devices. Each of the plurality of devices has a generally curved apical end and an opposing, generally concave coronal end. The apical end is configured to rest in a tooth-extraction socket and substantially conform to soft tissue of the tooth-extraction site immediately after a tooth has been extracted. The coronal end has a perimeter that is configured to substantially correspond and form a seal with gingival tissue surrounding the tooth-extraction site. The apical and coronal ends of each of the plurality of devices have (1) different shapes, each of the different shapes corresponding with a different tooth-extraction site location, or (2) substantially the same shape and different sizes.

In another embodiment described herein, a two-part gingival pontic device for developing a prosthetic tooth at a tooth-extraction site includes a gingival ovate pontic portion including a coronal end having a perimeter. The perimeter has a shape that forms gingival tissue surrounding the tooth-extraction site into an anatomical shape. The two-part gingival pontic device further includes a coronal pontic portion coupled to the gingival ovate pontic portion. The coronal pontic portion provides a visible part of the prosthetic tooth. The two-part gingival pontic device is located within a multi-tooth fixed dental prosthesis and fitting within the tooth-extraction site for preserving the gingival tissue.

In another embodiment described herein, a fixed dental prosthesis for mimicking at least two natural teeth includes a plurality of interconnected tooth-shaped portions. A first one of the interconnected tooth-shaped portions is a pontic device for fitting over an extraction site where a natural tooth has been extracted. A second one of the interconnected tooth-shaped portions includes an internal surface for engaging at least one of a natural prepped tooth or an abutment coupled to a dental implant. The pontic device is a formed by a two-part pontic assembly comprising a gingival pontic portion and a coronal pontic portion. The gingival pontic portion includes a dome-shaped structure having an anatomic shape for fitting within and preserving gingival tissue surrounding the extraction site. The coronal pontic portion is coupled to the gingival pontic portion and having a tooth shape.

The above summary of the embodiments described herein is not intended to represent each embodiment, or every aspect, of the present invention. This is the purpose of the figures and detailed description that follow.

BRIEF DESCRIPTION OF THE DRAWINGS

The foregoing and other advantages of the invention will become apparent upon reading the following detailed description and upon reference to the drawings.

FIGS. 12A-12G are side views of a portion of a patient's mouth showing a tooth extraction and placement of a 2-part pontic assembly, according to one embodiment.

Figure 1:
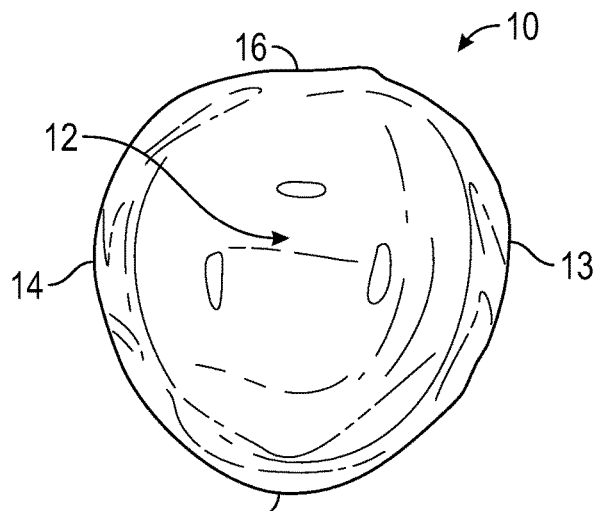
FIG. 1 is a gingival or apical-inferior view of a gingival ovate pontic according to one embodiment.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DESCRIPTION OF THE PREFERRED EMBODIMENTS

The embodiments discussed herein are directed to gingival ovate pontics configured to maintain and preserve soft and hard tissue at tooth-extraction sites and methods of using the same. As described herein, prefabricated, anatomic, and/or customized gingival forming methods may be used for preserving the anatomic tissue shape for restorations post-extraction in sites not receiving an implant.

Referring to FIGS. 1-7, a gingival ovate pontic 10 is shown according to one embodiment of the present invention. As illustrated in the gingival or apical view of FIG. 1, the gingival ovate pontic 10 has a closed, generally convex apical dome portion 12. The gingival ovate pontic 10 is configured to be placed at an outer surface of the gingival tissue around a soft tissue-extraction socket. As such, the dome portion 12, which is configured to generally rest in the extraction socket, generally anatomically mimics the shape of the extraction socket (dentogingival complex) that remains immediately after a tooth has been extracted and before the extraction socket begins to shrink, collapse, and/or shift from the natural size, shape, and position of its pre-extraction state. FIG. 1 also illustrates the mesial portion 13, the distal portion 14, the lingual portion 15, and the facial portion 16 of the gingival ovate pontic 10.

Figure 2:
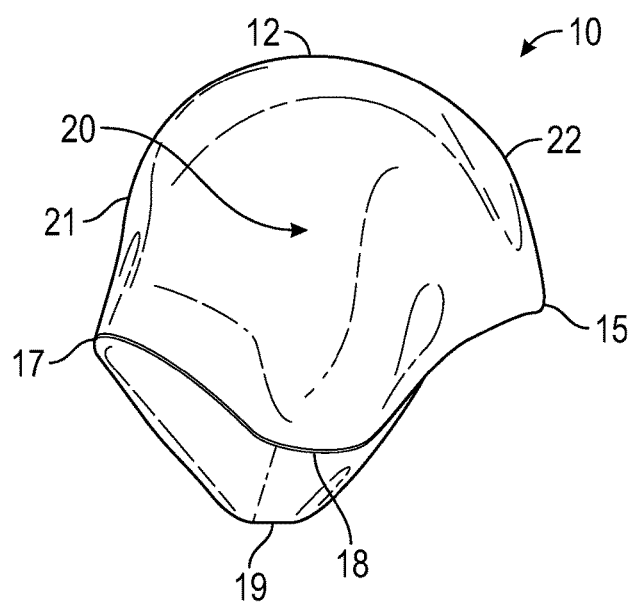
FIG. 2 is a distal view of the gingival ovate pontic of FIG. 1.

FIG. 2 illustrates a distal, perspective view of the gingival ovate pontic 10 of FIG. 1. As shown in FIG. 2, the perimeter of the gingival ovate pontic 10 at the coronal end is non-geometric and asymmetrically scalloped with opposing distal peaks 18 and mesial peaks 19 and opposing lingual and buccal portions 15, 17 positioned, respectively, between the peaks 18, 19, thereby mimicking the natural dentition. The distal peak 18 generally supports the distal papilla, and the mesial peak 19 generally supports the mesial papilla. The gingival ovate pontic 10 further includes a distal transition portion 20 that is configured to contact the junction of the soft tissues and/or the bony walls of the extraction socket. A buccal-distal interface 21 and a lingual-distal interface 22 are configured to contact the junction of the soft tissues and/or bony walls of the extraction socket.

Figure 3:
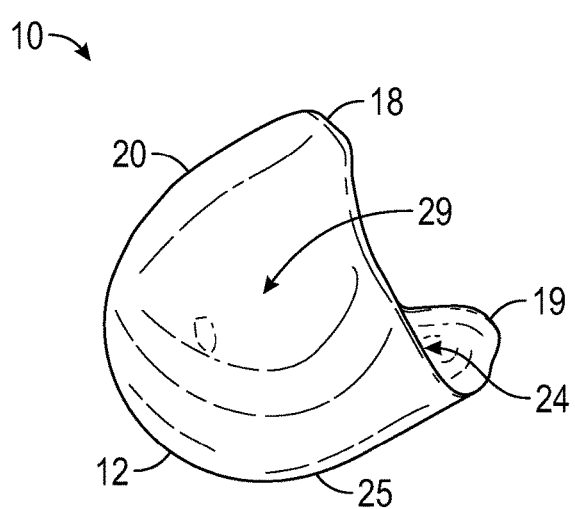
FIG. 3 is a distal-facial-apical perspective view of the gingival ovate pontic of FIG. 1.

FIG. 3 shows a distal-facial-apical aspect of the gingival ovate pontic 10 of FIGS. 1 and 2. A mid-facial transition interface 24 is configured to connect the gingival ovate pontic 10 to a coronal portion of an FDP. A mesial transition 25, the distal transition 20, and a facial transition 29 are configured to interface from the extraction socket to the soft tissue zone.

Figure 4:
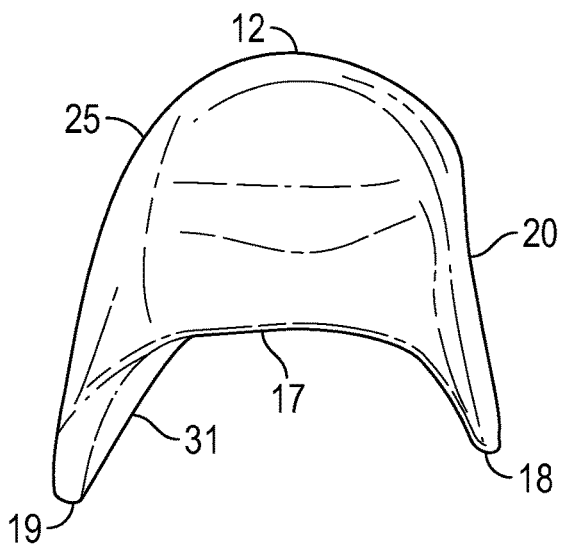
FIG. 4 is a facial or labial view of the gingival ovate pontic of FIG. 1.
Figure 5:
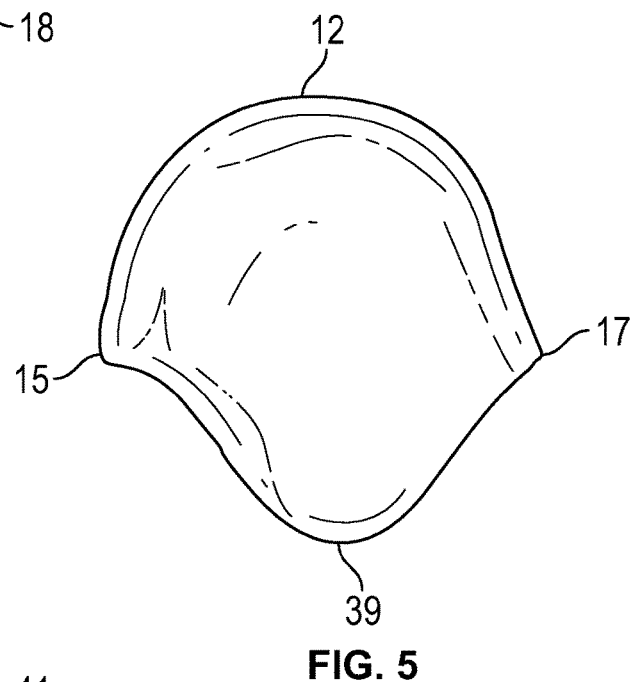
FIG. 5 is a mesial view of the gingival ovate pontic of FIG. 1.

FIG. 4 shows a facial aspect of the gingival ovate pontic 10 of FIGS. 1-3. A lingual interproximal portion 31 generally supports the lingual interproximal aspect of the papilla. The buccal portion 17 is configured to couple the gingival ovate pontic 10 to a coronal portion of the FDP. The lingual portion 15 (as shown in the mesial aspect view of FIG. 5) may further assist in connecting the gingival ovate pontic 10 to the coronal pontic (false tooth) portion.

Figure 6:
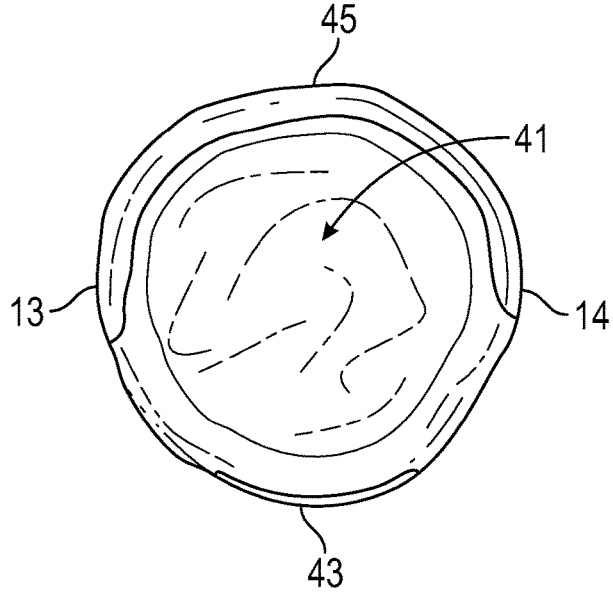
FIG. 6 is an occlusal view of the gingival ovate pontic of FIG. 1.

FIG. 6 illustrates an occlusal (coronal) aspect of the gingival ovate pontic 10. The gingival ovate pontic 10 includes a generally concave portion 41 positioned on the coronal end of the gingival ovate pontic 10, generally opposite to the dome portion 12. The perimeter of the generally concave portion 41 is substantially conformant in shape to the gingival tissues around the extraction site immediately following tooth extraction. The perimeter of the dome portion 12 is generally smaller than the perimeter of the generally concave portion 41 so that the device tapers outwardly from the perimeter of the dome portion 12 to the perimeter of the generally concave portion 14. A bucco-occlusal portion 45 generally has a larger area when compared to a lingual, inner perimeter 43 that comes into contact with the extraction socket.

Figure 7:
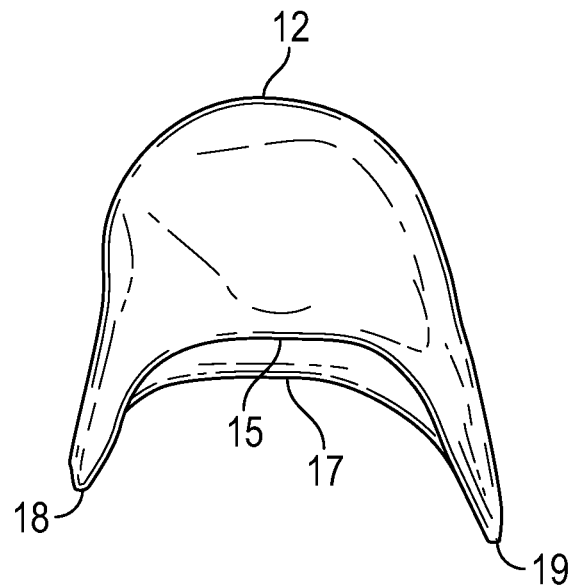
FIG. 7 is a lingual view of the gingival ovate pontic of FIG. 1.

FIG. 7 illustrates a lingual aspect of the gingival ovate pontic 10 of FIGS. 1-6. The dome portion 12 of the gingival ovate pontic 10 resides on top of the extraction socket to assist in inhibiting or preventing shrinkage of the extraction socket and/or to contain bone graft material, if so placed within the extraction socket. The lingual portion 15 and the buccal portion 17 assist in connecting the gingival ovate pontic 10 to the coronal or tooth portion of the FDP using a suitable restorative material(s).

As shown in FIGS. 1-7, the vertical height of the gingival ovate pontic 10 described herein is generally not uniform. For example, the interproximal surfaces at the distal peak 18 and the mesial peak 19 generally have greater heights than the buccal portion 17 and the lingual portion 15 of the gingival ovate pontic 10.

As also shown, in FIGS. 1-7, the gingival ovate pontic 10 described herein has an irregular solid design that generally mimics the shape of residual soft tissue of the extraction socket, e.g., the cross-sectional outline of a tooth root cervix in the extraction socket.

Figure 8:
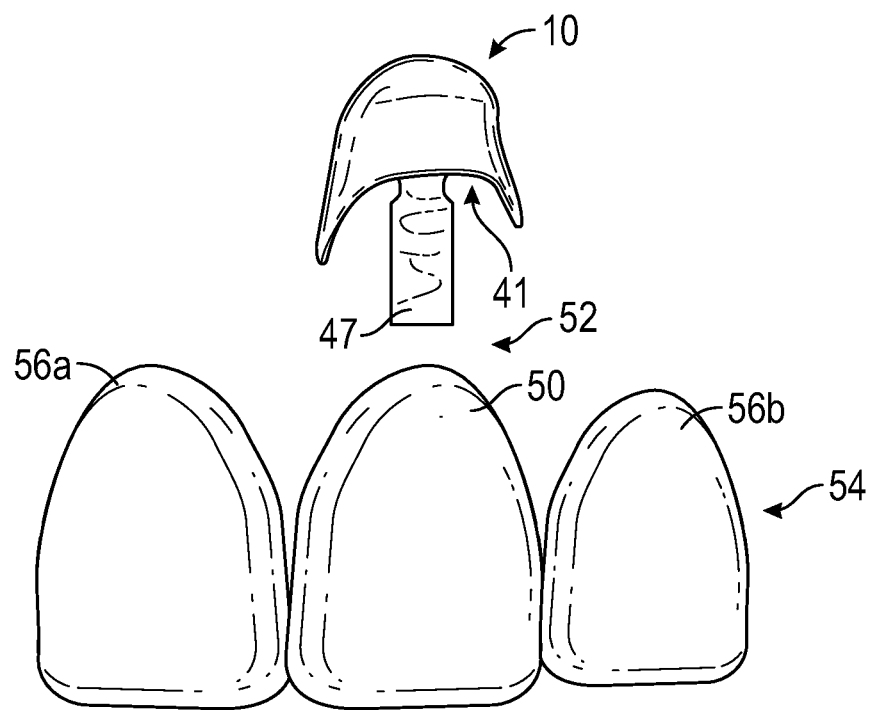
FIG. 8 shows a gingival ovate pontic with a tooth-borne or implant-borne 3-unit fixed dental prosthesis (FDP) including a two-part pontic assembly according to one embodiment.

Referring now to FIG. 8, a two-part pontic assembly 52 including the gingival ovate pontic 10 and a coronal pontic portion 50 is illustrated. The two-part pontic assembly 52 of FIG. 8 is shown as part of a tooth-borne or implant-borne 3-unit FDP 54. The FDP 54 generally mimics at least two natural teeth and includes a plurality of interconnected tooth-shaped portions, 50, 56a, 56b. The first one of the interconnected tooth-shaped portions is the coronal pontic portion 50 for fitting over an extraction site where a natural tooth has been extracted. At least one of the remaining interconnected tooth-shaped portions includes an internal surface for engaging at least one of a natural prepped tooth or an abutment coupled to a dental implant.

The coronal pontic portion 50 is coupled to the gingival ovate pontic 10 using any suitable material to create the two-part pontic assembly 52. The coronal pontic portion 50 may made of acrylic, other common dental plastics, or the like. In the embodiment of FIG. 8, the two-part pontic assembly 52 is adjacent to retainer abutments or crowns 56a, 56b of the tooth or implant-borne FDP 54.

As shown in FIG. 8, the gingival ovate pontic 10 is configured to be coupled to the coronal pontic portion 50 of the FDP 54 via a handle or protrusion 47 integrally formed into or coupled with and extending from the generally concave portion 41. The handle or protrusion 47 may include any suitable shape for receiving and holding the coronal pontic portion 50. For example, the protrusion 47 may have a length of about 2.0 mm, a width of about 3.5 mm, and a height of about 7.0 mm. In other embodiments, the generally concave portion 41 may include other structures or surface profiles to assist in coupling with the coronal pontic portion 50. For example, the generally concave portion 41 may include more than one protrusion extending coronally away from the generally concave portion 41. In some embodiments, the protrusion 47 includes a tooth-identifying code for indicating the tooth number for which it is intended for use, the orientation of the gingival ovate pontic 10 within the extraction socket, combinations thereof, or the like.

In addition to assisting with coupling the gingival ovate pontic 10 with the coronal pontic portion 50, the protrusion 47 may assist a clinician in easily placing the gingival ovate pontic 10 into the extraction socket after the tooth has been extracted. In some embodiments, the protrusion 47 may have a textured (e.g., ridged) surface, thereby assisting in preventing slipping when the gingival ovate pontic 10 is being held or transferred. Preferably, the protrusion 47 extends beyond the distal peak 18 and the mesial peak 19 on the gingival ovate pontic 10. While the gingival ovate pontic 10 in FIGS. 1-7 is shown without a protrusion, the present invention contemplates the gingival ovate pontic 10 with and without a protrusion 47.

The gingival ovate pontic 10 has an exterior surface that is substantially conformant in shape to the gingival tissue around a tooth-extraction site immediately following tooth removal. The perimeter generally contacts the dentogingival complex tissues such that minimal or no spaces or gaps exist between the gingival ovate pontic 10 and the surrounding gingival tissue.

Figure 9A:
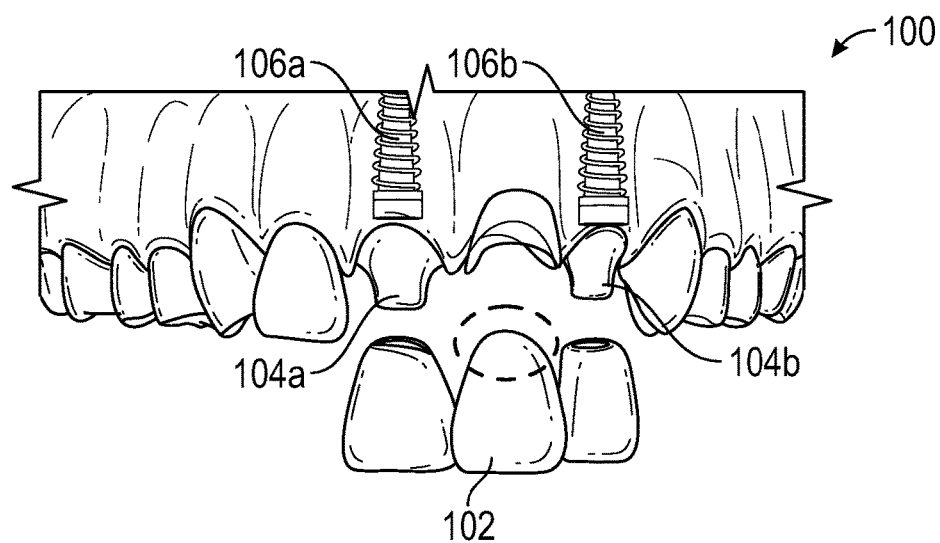
FIG. 9A illustrates an FDP including a two-part pontic assembly supported by two abutments, which are coupled to two respective dental implants.

FIGS. 9A-9G illustrate various clinical situations in which an FDP may be used. In FIG. 9A, a 3-unit FDP 100, which includes a two-part pontic assembly 102 is supported on either side by a respective abutment 104a, 104b, which is coupled to a respective dental implant 106a, 106b.

Figure 9B:
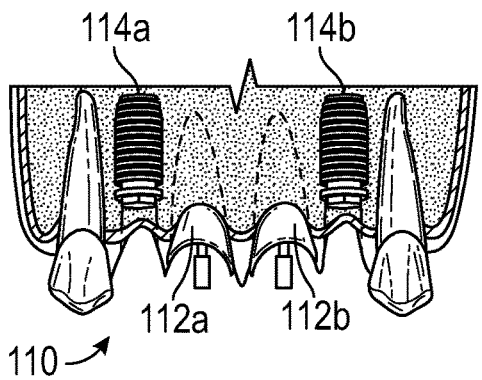
FIG. 9B-9E illustrate various examples of edentulous mouth regions with which the gingival ovate pontics described herein may be used.

FIG. 9B illustrates an edentulous region 110 for receiving a 4-unit FDP (not shown). The edentulous region 110 includes two gingival ovate pontics 112a, 112b placed into adjacent extraction sockets. Coronal pontic portions of the 4-unit FDP may be coupled to a respective gingival ovate pontic 112a, 112b and supported by two abutments (not shown) coupled to two respective dental implants 114a, 114b.

Figure 9C:
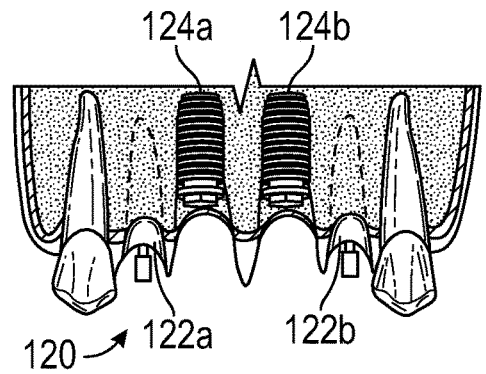

FIG. 9C illustrates an edentulous region 120 for receiving a 4-unit FDP (not shown) according to another embodiment. The edentulous region 120 includes two gingival ovate pontics 122a, 122b placed into non-adjacent extraction sockets. Coronal pontic portions of the 4-unit FDP may be coupled to a respective gingival ovate pontic 122a, 122b such that the generally central portion of the FDP is anchored by abutments (not shown) coupled to respective dental implant 124a, 124b placed between the two gingival ovate pontics 122a, 122b. As such, the coronal pontic portions of the 4-unit FDP would be "cantilevered" on either end of the 4-unit FDP.

Figure 9D:
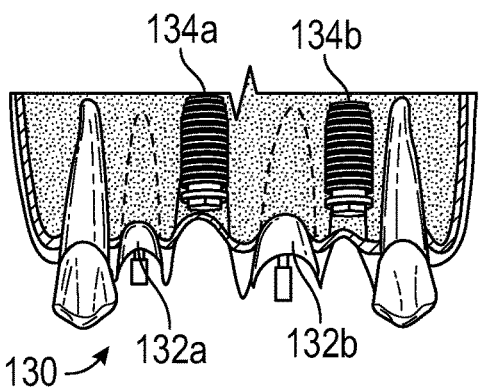

FIG. 9D illustrates an edentulous region 130 for receiving a 4-unit FDP (not shown) according to another embodiment. The edentulous region of FIG. 9D includes two gingival ovate pontics 132a, 132b and two dental implants 134a, 134b positioned in alternating locations of the edentulous region 130. Coronal pontic portions of the 4-unit FDP may be coupled to a respective gingival ovate pontic 132a, 132b. The 4-unit FDP may be supported by a first abutment coupled to the first dental implant 134a and a second abutment 134b coupled to the second dental implant 134b.

Figure 9E:
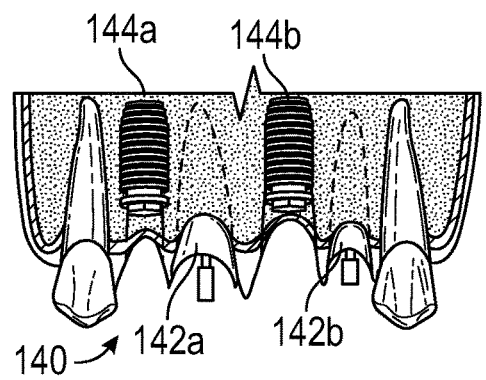

FIG. 9E illustrates an edentulous region 140 for receiving a 4-unit FDP (not shown) according to yet another embodiment. The edentulous region 140 of FIG. 9E includes two dental implants 144a, 144b and two gingival ovate pontics 142a, 142b positioned in alternating locations of the edentulous region 140. Coronal pontic portions of the 4-unit FDP may be coupled to a respective gingival ovate pontic 142a, 142b. The 4-unit FDP may be supported by first and second abutments coupled to a respective first and second dental implant 144a, 144b.

Figure 9F:
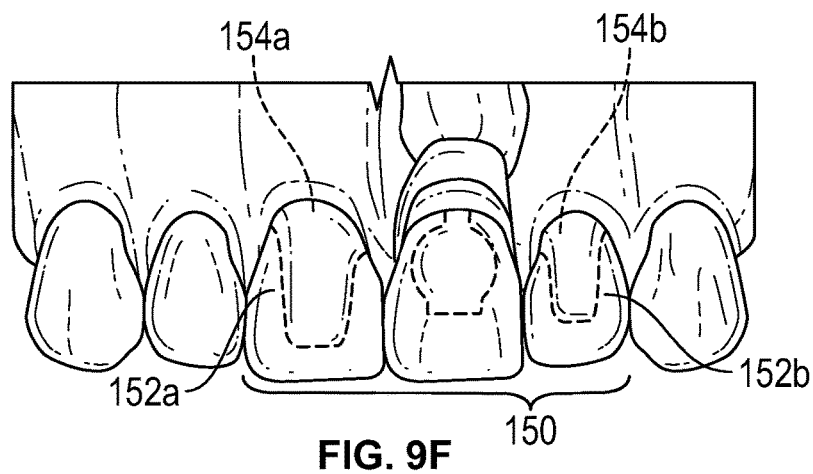
FIG. 9F illustrates a side view of a tooth-anchored 3-unit FDP.

Referring now to FIG. 9F, a tooth-borne 3-unit FDP 150 is shown. Both ends 152a, 152b of the FDP 150 are coupled to crowns positioned on adjacent teeth 154a, 154b.

Figure 9G:
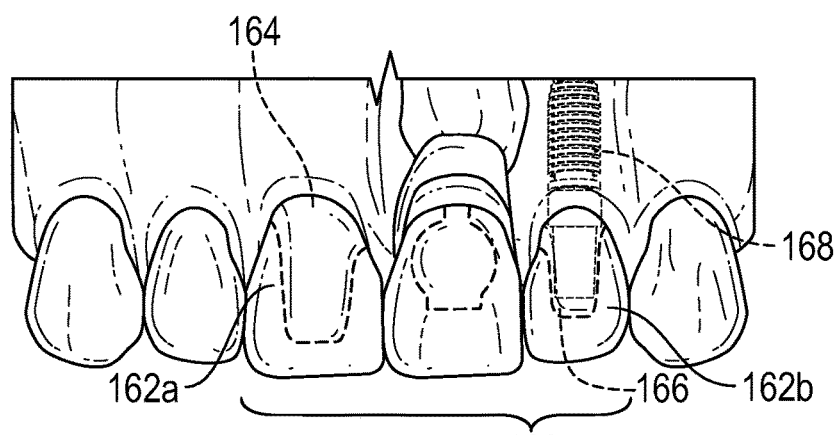
FIG. 9G illustrates a side view of a tooth- and implant-anchored 3-unit FDP.

FIG. 9G illustrates a 3-unit FDP 160 that is partially tooth-borne and partially implant-bone. More specifically, a first side 162a of the FDP 160 is coupled to a crown positioned on an adjacent tooth 164, and a second opposing side 162b of the FDP 160 is coupled to an abutment 166, which is attached to a dental implant 168.

Portions (e.g., the emergence profiles) of the gingival ovate pontic 10 may be over-contoured or under-contoured relative to the respective portions of the extraction socket. For example, one or more portions/surfaces of the gingival ovate pontic 10 may be over-contoured to enhance the ability to place and angulate the gingival ovate pontics 10. This assists in ensuring physical contact along all or most aspects of the soft tissue of the extraction socket to reestablish an effective biologic seal between the outer surface of the gingival ovate pontic and the residual soft tissue perimeter. The supra-gingival contour of the gingival ovate pontic 10 and/or the coronal pontic portion 50 may be substantially identical to the natural tooth, while the sub-gingival contour may possess an emergence profile contour that is either over-contoured or under-contoured to compensate for the extraction site and natural tooth anatomy.

It may also be desirable for the clinician to modify the shape and/or surface of the gingival ovate pontic 10 to properly adapt to the soft tissue of the extraction socket, e.g., in situations where the patient has an unusual anatomy. Techniques whereby material is added or subtracted from a standard gingival ovate pontic may be used. In some embodiments, the gingival ovate pontic 10 may be modified "chair side" by the clinician.

The gingival ovate pontic 10 described herein may be immediately placed at the time of tooth extraction to reestablish an effective biologic seal of the soft tissue to the surface of the gingival ovate pontics 10 and/or to maintain the pre-extraction anatomic shape of the soft tissue at the tooth-extraction site. The gingival ovate pontic 10 may extend from the crest of bone in about 360 degrees to the height of the remaining soft tissue.

Anatomically, the gingival ovate pontic 10 described herein generally has shapes and dimensions that correspond with the gingival end of the coronal pontic portion 50 that is to be coupled thereto. As such, the gingival ovate pontics 10 described herein may be used as a foundation for a temporary prosthetic tooth for immediate cosmetic replacement of an extracted tooth.

As shown, for example, in FIG. 8, the coronal pontic portion 50 of the FDP 54 is generally coupled to the perimeter of the generally concave portion 41 at the coronal end of the gingival ovate pontic 10. The gingival ovate pontic 10 generally does not depend upon the physical, anatomic, or functional location of the coronal part of the coronal pontic portion 50. Consequently, the gingival ovate pontic 10 described herein can be used to shape and contour the gingival soft tissue aspect of a healed or augmented edentulous ridge for a false tooth pontic independent of the coronal part of the pontic portion 50.

The methods and devices described herein assist in providing structural support to and preserving the soft tissue architecture of the gingival tissue surrounding the gingival ovate pontic 10. Specifically, the gingival ovate pontic 10 may be used to assist in shaping and contouring the gingival architecture of a tooth-extraction site. For example, the gingival ovate pontic 10 may be used to create the soft tissue shape of the gingival tissue in a healed or augmented edentulous ridge site for delayed cosmetic replacement of an extracted tooth. The gingival ovate pontic 10 allows for a quick, anatomically correct "scaffold" to help support the gingiva after tooth extraction. The well-designed subgingival contours of the gingival ovate pontic conform to the pre-extraction state of the tooth root cervix.

According to some embodiments, the gingival ovate pontic 10 described herein may be prefabricated in a variety of sizes to be tooth-specific, e.g., to match the location/position of the particular tooth that has been extracted. Each gingival ovate pontic 10 may be manufactured in generally standardized (digital) shapes and dimensions that generally mimic the root cervical surface of the extracted tooth and the soft tissues of a particular extraction socket location associated with each of the 28 teeth of a patient's mouth (e.g., based on tooth number). As such, the devices and methods described herein are unique in that they are tooth-specific for capturing the supragingival tissues of an extraction socket and substantially anatomically mimicking the cervical portion of the tooth root cervix to maintain the contours, shape, and volume of the dentogingival complex following tooth removal. Thus, the gingival ovate pontic 10 may substantially or completely fill the soft tissue zone of the extraction socket.

The gingival ovate pontic 10 described herein may be prefabricated in a variety of sizes and complementary shapes of the tooth root cervical surfaces to contour and shape a healed or augmented edentulous ridge site that will receive the two-part pontic assembly.

Figure 10:
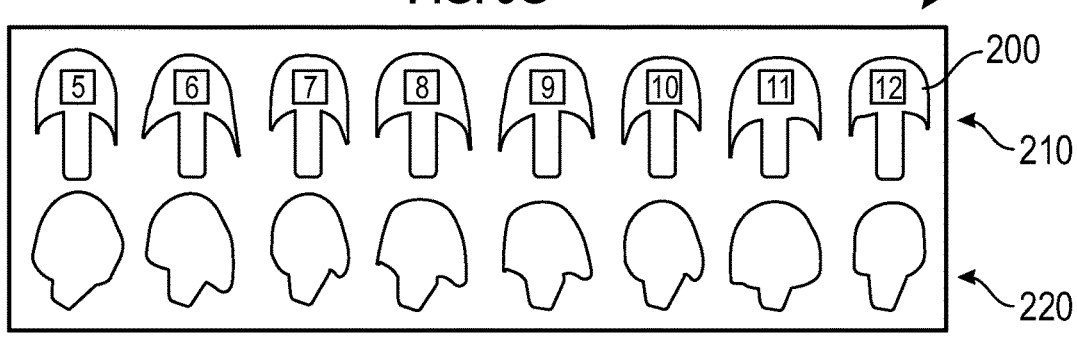
FIG. 10 illustrates various views of a kit of gingival ovate pontics configured to be used in different tooth extraction locations in a patient's mouth.

The gingival ovate pontic devices 10 described herein may be supplied in a kit that includes one or more gingival ovate pontic devices 10 per tooth-extraction site location in a patient's mouth, as shown in FIG. 10. Each tooth to be removed (and corresponding tooth-extraction site location) corresponds with a gingival ovate pontic device having a different shape and/or dimension associated therewith. As such, a kit may be provided that includes a plurality of gingival ovate pontic devices, each of which corresponds with a respective tooth-extraction site location.

A plurality (e.g., a kit) of gingival ovate pontic devices may also be provided for a single tooth-extraction site location, where each of the plurality of devices is more patient-specific. For example, a plurality of gingival ovate pontic devices of varied sizes may be supplied having the same general shape, thereby being configured for use in the same tooth-extraction site location. A dental clinician may select an appropriate size more customized to a particular patient, since tooth and tooth-extraction site sizes will vary among individuals.

Accordingly, a gingival ovate pontic device may be selected such that the selected gingival ovate pontic device corresponds with (1) the tooth to be removed/tooth-extraction site location and/or (2) the size/dimensions best suited for the specific patient in which the gingival ovate pontic device is to be placed. Once a proper gingival ovate pontic device is selected from the variety of types and/or sizes, it may be placed within the tissue zone of the extraction socket.

FIG. 10 illustrates one example of a kit 195 including a plurality of gingival ovate pontics 200. The first and second rows 210, 220 of FIG. 10 illustrate facial and facial-occlusal views, respectively, of the gingival ovate pontics 200. From left to right, the illustrated gingival ovate pontics 200 are configured to be used in a tooth-extraction site corresponding with location #5 (bicuspid), #6 (canine), #7 (lateral incisor), #8 (central incisor), #9 (central incisor), #10 (lateral incisor), #11 (canine), and #12 (bicuspid). Put another way, each column of FIG. 10 shows a tooth-specific gingival ovate pontic 200 used to replace one of teeth #5-12. Each of the gingival ovate pontic devices 200 is may be modifiable, predominantly in length, by a clinician to match the tooth-extraction site of the prevailing conditions in the patient's mouth. In other words, the kit 195 of gingival ovate pontics 200 provides the clinician with some flexibility in selecting the best gingival ovate pontic for a certain tooth, but the clinician may still perform some modifications to make the gingival ovate pontic even more patient-specific. Each of the plurality of gingival ovate pontics in the kit may be coupled to a corresponding coronal pontic portion of an FDP.

Figure 11:
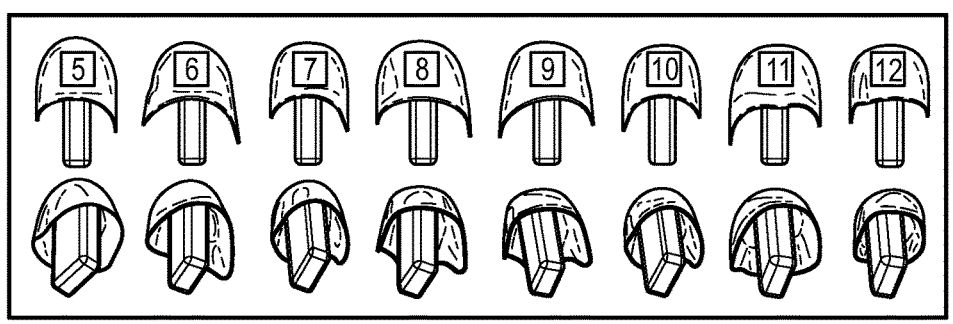
FIG. 11 illustrates digital images (e.g., from stereolithography (STL) files) corresponding with the devices of FIG. 10.

FIG. 11 illustrates images derived from and/or corresponding to digital files corresponding to the gingival ovate pontics 200 of FIG. 10 for ease of manufacturing. In one embodiment, the files are in a stereolithography (STL) format so that they may be produced from, e.g., a rapid-prototyping manufacturing technique. STL files are generally associated with volumetric dimensions for the digital (e.g., CAD/CAM) fabrication of the gingival ovate pontics. STL files are 3-dimensional CAD/CAM (computer-aided design/computer-aided manufacturing) files stored in a computer database. The STL files may be used to create physical pieces of the gingival ovate pontics 200. The STL files are generally tooth-specific, accounting for all of the teeth in the dentition of both jaws, generally with the possible exception of the third molars (28 in total). Existing systems may employ a block of material (e.g., acrylic or composite) and, through subtractive milling with coordinated spinning drilling tips, fabricate one or more of the gingival ovate pontics 200 in its full complete form. It is contemplated that other technologies may also "print" one or more of the gingival ovate pontics 200 using, e.g., rapid-prototyping manufacturing techniques and/or 3D printing machines, which may add sequential layers of material by spraying onto a substrate and then polymerizing and/or curing with a light-activated source.

The embodiments of the present invention also contemplate developing patient-specific dimensions and shapes for the gingival ovate pontic. For example, an intraoral scan of the mouth before and/or after the tooth extraction may provide specific dimensions and shapes to be used in creating the gingival ovate pontic (or to select the most ideal sized/shaped gingival ovate pontic to be used on the patient from a library of electronic files for the gingival ovate pontic). Additionally or alternatively, the extracted tooth can be imaged, and the detailed geometry of the gingival region can be determined from the extracted tooth to be used in the development of a patient-specific gingival ovate pontic.

One advantageous feature of the gingival ovate pontics described herein is their ability to form an effective biologic socket seal between the surface of the soft tissue of the extraction socket and the gingival ovate pontic to adequately support and seal the residual soft tissue socket at the time of placement. The gingival ovate pontics may provide a single uniform material within the soft tissue zone of the extraction socket that inhibits or prevents microscopic gaps and macroscopic gaps between dissimilar materials in the soft tissue gingival zone. As such, the biologic seal may inhibit or preclude bacteria and environmental contaminants from invading the soft tissues and bony sockets of a tooth-extraction site.

In some embodiments, the gingival ovate pontics described herein may be confined to the transmucosal (tissue zone) region extending from the crest of the bone to the free gingival margin. In other embodiments, the gingival ovate pontics may continue to extend into the oral cavity as the labial surface of material to replace the labial surface of the removed tooth.

In some embodiments, at least a portion of the gingival ovate pontic 10 (e.g., the generally curved apical, underside portion) includes or is coated with a bio-compatible material for promoting healing and soft tissue adherence, thereby expediting engagement of the soft tissue socket within the tooth-extraction site. The gingival ovate pontic and the gingival surface may be a platform or substrate for addition of biological materials, which may create a hybrid biological device design. In some embodiments, the surface of the gingival ovate pontic can be coated with one or more biologic/biocompatible materials such as collagen to promote healing and soft tissue adherence, expediting and creating the biologic seal. The biocompatible material may include, for example, a dense collagen, collagen-coated acrylic, or the like. In one embodiment, the gingival ovate pontic may be non-resorbable at one (e.g., coronal) end and at least partly resorbable at the opposing (e.g., apical) end. The biologic material may be sprayed or otherwise applied.

The gingival ovate pontics may be luted to FDPs, ceramic teeth, bridges, or the like with, e.g., laboratory resin cement, collagen-containing substances, or the like.

Prior to extraction, a clinical photo can be taken of the tooth to be extracted to allow future comparison of the pre-treatment condition to the post-operative outcome. The photo may include a reference measurement tool and/or an instrument for analyzing soft tissue changes.

A dental impression may be used as a generally accurate representation of the teeth and surrounding gingival tissues. The dental impression may be formed using conventional impression materials such as, for example, alginate, polyether, vinyl polysiloxane, other suitable materials, or any combination thereof. A dental impression may also be a digital impression such as cone-beam computer tomography or digital oral impression (CAD/CAM digital impressions) using, for example, a hand-held oral scanning device. The dental impression may then be used to form the FDP to be used with the gingival ovate pontic(s).

Care is generally taken to preserve the entire tissue zone and minimize trauma to the supporting gingival tissues during each phase of treatment. As discussed above, it is important to preserve the soft tissue architecture of the immediate and surrounding gingival tissues to preserve the aesthetic appearance and to reestablish a biologic seal with the gingival ovate pontic after the tooth is removed. As such, a "flapless" surgical technique (without flap elevation) may be used.

Referring now to FIGS. 12A-12G, a series of side views of a tooth-extraction site 300 are shown according to one method. If the FDP to be used in the extraction site 300 is to be tooth-borne (see FIG. 9F) or partially tooth-borne (see FIG. 9G), the tooth or teeth adjacent to the extraction site (e.g., teeth 302a, 302b of FIG. 12A) may be prepared. For example, the adjacent teeth 302a, 302b may be milled such that an anchoring crown may be placed thereon. It may be desirable to prepare the adjacent teeth 302a, 302b prior to tooth extraction such that debris from milling the adjacent teeth 302a, 302b does not enter into the resulting extraction socket.

A gingival ovate pontic 306 having proper vertical and horizontal dimensions may also be selected. As discussed above, gingival ovate pontics may be supplied in various dimensions corresponding with the tooth to be replaced.

Next, a tooth 304 that is to be extracted may be prepared. The supra-crestal attachment (i.e., the soft tissue socket) of the tooth 304 that is to be extracted may be carefully incised around the tooth 304 to surgically disconnect the gingival fibers from the tooth cervical root surface. The method generally requires careful dissection of the supra-crestal attachment, which includes the sulcular epithelium, junctional epithelium, and connective tissue-inserting fibers that are found between the connective tissue and the surface of the root above the crest of the bone.

Once the supra-crestal fibers are released, the superior periodontal ligament fibers (e.g., the attachment fibers between the alveolar bone socket and root surface) can be incised. The superior periodontal ligament fibers should be severed using minimal disruption to the surrounding soft tissue and/or bony architecture. A surgical instrument may be placed into the entrance of the periodontal ligament between the tooth 304 and inner socket wall. The periodontal attachment fibers may then be severed around the tooth 304 to a depth of about 1 mm to about 4 mm, depending on the ease of entry into the periodontal ligament space.

Referring now to FIG. 12B, extraction of the tooth 304 may be initiated using a rotational movement in order to detach the remaining subcrestal periodontal fibers fastening the tooth 304 to the inner socket wall. Once a rotational movement is achieved, a vertical force may be applied to the tooth 304 to advance the root out of the bony socket. When extraction is performed this way, disruption to the surrounding soft tissue of the gingival zone may be minimized. The interdental papillae are not or are minimally surgically altered from the pre-extraction state condition, and incisions that compromise the blood supply to the region of the bone and surrounding soft tissue vascular complex are generally eliminated. The architecture of the soft tissue is generally unaltered other than the severing of the intrasulcular gingival attachment fibers between the tooth root surface and the inserting fibers.

In some methods, inflammatory granulation tissue may be removed from within the resulting extraction socket 308. The integrity of the remaining inner socket walls of the extraction socket 308 (see FIG. 12C) may be inspected. For example, a radiograph may be taken to determine the post-extraction configuration of the extraction socket 308. This step may be referred to as preparing the bony socket or extraction socket.

Once the proper gingival ovate pontic 306 has been selected from the variety of sizes and diameters, it may be placed within the extraction socket 308, as shown, for example, in FIG. 12D. The placement may be done using an instrument that grips a protrusion 310 extending from the coronal end of the gingival ovate pontic 306. The outer perimeter of the coronal end of the gingival ovate pontic 306 makes physical contact with the gingival tissue, as shown in FIG. 12E, ensuring a biologic seal between the soft tissue and surface of the gingival ovate pontic 306. In some embodiments, the gingival ovate pontic 306 fits into the extraction socket 308 with generally passive contact, without applying excessive pressure at any specific point or area in the extraction socket 308. A coronal pontic portion 320 of an FDP 322 may then be coupled to the gingival ovate pontic 306, as shown in FIGS. 12F and 12G.

In one embodiment, the coupling is done using a provisional restorative material that is initially flowable such as polymethymethacrylate (PMMA), acrylic, bisacrylic, composite resin, any combination thereof, or the like. The material may then harden to form the two-part pontic assembly. For example, the provisional restorative material may be added to an opening in the interior of the coronal pontic portion 320, and the protrusion 310 may be subsequently inserted into the opening, thereby attaching the gingival ovate pontic 306 to the coronal pontic portion 320. A resulting two-part pontic assembly 330 may then be cleaned, trimmed, polished, or the like.

Optionally, a hard-tissue (e.g., bone) grafting material may be added into the extraction socket 308. The bone graft material may include autografts, allografts, xenografts, alloplastic grafts, and/or a variety of bone replacement and cell stimulating materials that may include bone morphogenic proteins (BMPs), stem cell derivatives, platelet rich proteins (PRPs) derived from a patient's blood, and/or other biological sources or combinations thereof.

The gingival ovate pontic 306 generally functions as a physical barrier for containing the hard-tissue graft material. Maintenance of the graft material with the gingival ovate pontic 306 during the maturation cycle of bone formation may be important for edentulous ridge shape preservation and in minimizing collapse.

After being attached to the coronal pontic portion and being anchored to the adjacent teeth and/or implants, the resulting two-part pontic assembly 330 (see FIGS. 12F-12G) may be placed back into the patient's mouth, namely, by inserting the gingival ovate pontic 306 portion of the two-part pontic assembly 330 back into the extraction socket 308 of the patient's mouth. The gingival ovate pontic 306 may be left in place in the extraction socket 308 from about 3 months to about 5 months. The duration of time may be shorter, or it may be longer in instances in which, e.g., a hard tissue regenerative material has been placed into the extraction socket such that the hard and soft tissues are allowed to heal and mature. As such, the gingival ovate pontic 306 also serves the purpose of helping to retain the hard tissue regenerative material within the extraction socket 308.

Figure 13:
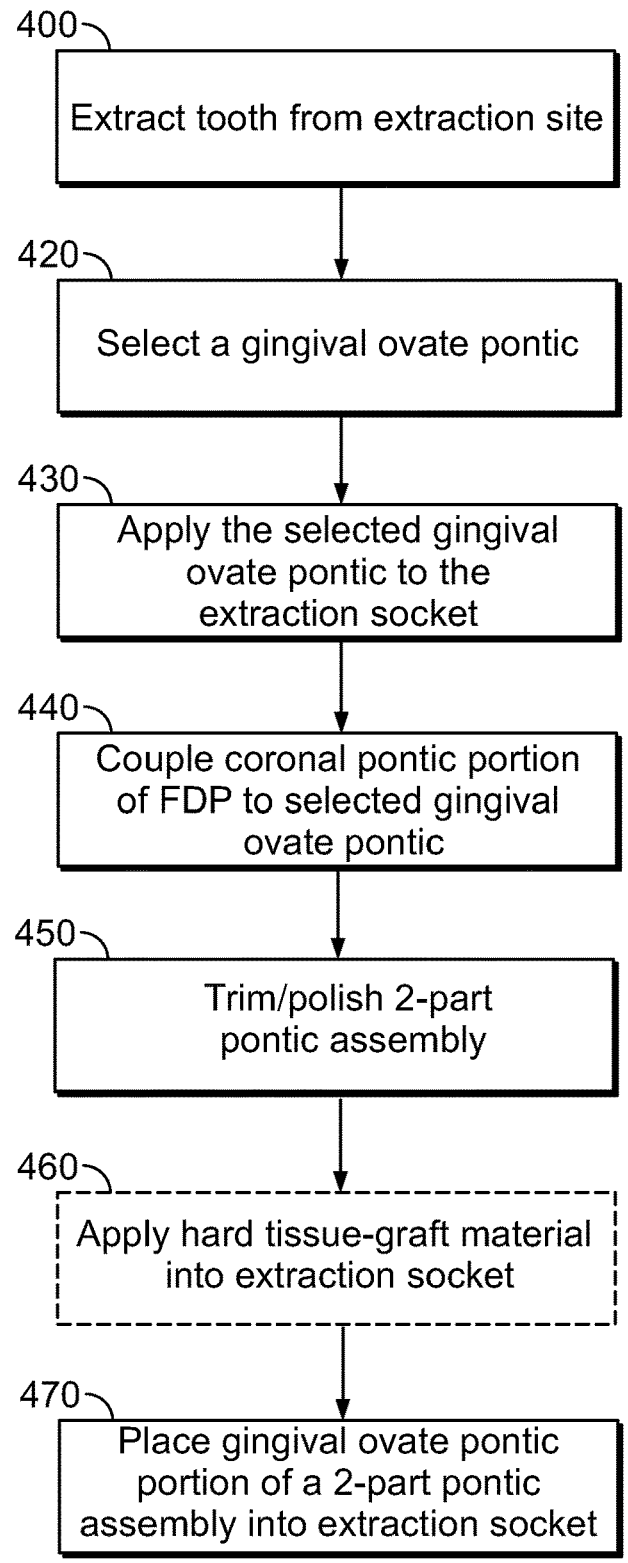
FIG. 13 illustrates an example of a dental restoration method in accordance with the embodiments described herein.

A dental restoration method according to one embodiment is illustrated in FIG. 13. At step 400, a dental restoration method includes extracting a tooth from a tooth-extraction site, where the tooth-extraction site has gingival tissue surrounding the tooth. The extraction results in an extraction socket having soft and hard tissue positioned therein. A gingival ovate pontic may then be selected at step 420. The method further includes applying the selected gingival ovate pontic to the extraction socket at step 430. The method further includes coupling a coronal pontic portion of an FDP to the selected gingival ovate pontic to create a two-part pontic assembly at step 440. The two-part pontic assembly may be trimmed, polished, or the like at step 450. At optional step 460, a hard tissue-grafting material may be applied into the extraction socket. The gingival ovate pontic portion of the two-part pontic assembly may then be inserted into the extraction socket at step 470. The FDP may be anchored to adjacent teeth or to abutments supported by dental implants.

The methods described herein generally support the soft tissue submergence profile, allowing for better, more natural healing and aesthetics. The methods also help protect the blood clot and healing process.

The gingival ovate pontics described herein may be used in lieu of conventional membranes for immediate post-extraction socket ridge preservation in, e.g., Type 1 (intact) extraction sockets.

It is contemplated that the gingival ovate pontics described herein may be used in combination with a membrane and/or a bone graft, which may be useful for, e.g., for Type 2 (labial plate dentoalveolar dehiscence defects) extraction socket reconstruction. In these embodiments, the membrane can be placed at the level of the bony crest of the extraction socket. Placement of the gingival ovate pontic over the membrane may assist in providing generally complete coverage of the underlying membrane such that a biologic seal to the outer oral environment is formed (provided that a bony wall (e.g., buccal dehiscence defect) is absent).

The overlying gingival and surrounding soft tissues in a tooth extraction zone may thus be preserved by implementing several critical factors: (1) a minimally invasive surgical approach; (2) preservation of soft tissue architecture; and (3) reestablishing the blood supply to the surrounding tissues.

Each gingival ovate pontic has a series of externally defined dimensions including a tissue zone height, generally ranging from about 2.0 mm to about 5.0 mm. The gingival ovate pontics may be provided in several root form configurations and horizontal widths.

Non-limiting examples of horizontal dimensions for a maxillary right central incisor, a maxillary right lateral central incisor, a maxillary right canine, a maxillary left central incisor, a maxillary left lateral central incisor, and/or a maxillary left canine include heights of about 2 mm, about 3 mm, or up to about 5 mm, small, medium, or large diameters, and irregular asymmetric superior surfaces for generally conforming to the soft tissue gingival architecture. The dimensions associated with the interproximal points may be greater than those of the labial and lingual surfaces.

According to some embodiments, the gingival ovate pontics described herein may include a surgically sterile surface with a bi-layer micro-texture to assist in promoting immediate soft-tissue repair and reattachment to the biologic surface. It is contemplated that the gingival ovate pontic surface may have a non-uniform, irregular micro-geometric porous pattern. It is also contemplated that the surface texture may be modified using, e.g., a rotary or other suitable instrumentation or manufacturing process.

In some embodiments, the outer surface design of the gingival ovate pontic may possess more than one surface topography or texture region. For example, the superior (coronal) surface region may be smooth to discourage the accumulation of plaque. The smooth superior zone may extend from about 1 mm to about 3 mm. The inferior (apical) region may include micro-porous surface irregularities, textures, or patterns. The inferior micro-porous region may cover the remaining outer surface and generally encourages the reestablishment of the gingival fibers to contact and adhere to the inferior or apical surface of the gingival ovate pontic. As such, the micro-porous surface assists in promoting and accelerating effective cellular soft tissue adhesion to the surface, promoting soft tissue preservation, and providing an effective biologic seal of the surface of the device to the residual soft tissues. This encourages superficial layers of the dermis to adhere to a smooth superior region of the gingival ovate pontic and encourages functional fiber orientation to the roughened inferior region to promote a functional connective tissue attachment.

In other embodiments, the surface of the gingival ovate pontic may have a single texture. For example, the entire surface of the gingival ovate pontic may be smooth or micro-porous. Alternatively, the surface of the gingival ovate pontic may include multiple (e.g., more than two) textures, for example, to encourage direct soft tissue adaptation within the tissue zone. The surface of the device may be also treated by, e.g., steam cleaning or disinfection.

The gingival ovate pontics described herein may be formed of a variety of biocompatible materials including, but not limited to, acrylic, bisacrylic, composite, polycarbonate, ceramic, lithium disilicate, disilicate polyetheretherketone (PEEK), zirconia and other crystalline structures, other suitable materials, or any combination thereof. For example, they may be milled or sintered from high strength ceramic materials. It is contemplated that the material(s) may be anti-microbial and/or bacteriostatic to assist in retarding the growth or colonization of microorganisms on the surface of the gingival ovate pontic. Non-limiting examples of such anti-microbial and/or bacteriostatic materials include silver, copper, magnesium, titanium, hydroxyapatite, combinations thereof, or the like. These materials can be incorporated into the device material or may be applied to the device surface forming, e.g., a second layer or coating.

It is contemplated that the gingival ovate pontics described herein may not be confined to the tissue zone. Rather, in other embodiments, the gingival ovate pontic may include part of all of the tooth form that was extracted.

In summary, the gingival ovate pontics described herein have several advantages. First, the gingival ovate pontics generally assist in preserving the soft tissue architecture after the immediate removal of a tooth and in supporting the hard and soft tissues to prevent collapse of bone and soft tissue during healing. The gingival ovate pontics also create a physical and biologic soft tissue seal with the surrounding soft tissues to inhibit or prevent contaminants from entering the extraction socket. The seal may also serve to protect bone graft material that may be added to the extraction socket post-extraction. Additionally, the gingival ovate pontics may enhance soft tissue adhesion by providing direct physical contact between the prosthesis and the surrounding soft tissue socket. Thus, the gingival ovate pontics may assist in providing extraction socket preservation and/or hard tissue graft containment immediately following tooth removal.

The gingival ovate pontics described herein can be used in extraction sockets adjacent to teeth (i.e., tooth-tooth). They may also be used in conjunction with tooth-implant borne restorations.

As discussed above, epithelial and connective tissue cells may adhere or attach to material surfaces, thereby creating a true cell-mediated biologic seal. Once this biological seal is established in the early healing phase of extraction site treatment, bacteria and foreign substances are inhibited or precluded from entering this area. The gingival ovate pontic soft tissue contact surface area has a microstructure/texture/micro-porosity that assists in creating a physical platform/scaffold for soft tissue (e.g., epithelium and/or connective tissue) adherence.

Gingival ovate pontics, as described herein, may be used to shape and form the gingival contours of the soft tissues in a healed or augmented edentulous ridge site that is to receive an ovate pontic.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A two-part gingival pontic device for developing a prosthetic tooth at a tooth-extraction site, comprising:
   a gingival ovate pontic portion including a coronal end having a perimeter, the perimeter having a shape that forms gingival tissue surrounding the tooth-extraction site into an anatomical shape, the gingival ovate pontic portion further including a generally curved apical portion forming a solid, uninterrupted distal end generally opposite the coronal end, the distal end being configured to removably rest in a tooth extraction socket, the apical portion being configured to substantially conform to soft tissue of the tooth-extraction site immediately after a tooth has been extracted; and
   a coronal pontic portion coupled to the gingival ovate pontic portion, the coronal pontic portion providing a visible part of the prosthetic tooth, the two-part gingival pontic device being located within a multi-tooth fixed dental prosthesis and fitting within the tooth-extraction site for preserving the gingival tissue, the multi-tooth fixed dental prosthesis including the coronal pontic portion and at least one adjacent tooth-shaped portion, the at least one adjacent tooth-shaped portion including an internal surface for engaging at least one of a natural prepped tooth or an abutment coupled to a dental implant.

2. The device of claim 1, wherein the perimeter of the coronal end inhibits bone-grafting material from exiting the tooth-extraction site.

3. The device of claim 1, wherein the gingival ovate pontic portion includes at least one protrusion extending away from the coronal end, the coronal pontic portion fitting around the at least one protrusion.

4. The device of claim 3, wherein the at least one protrusion includes a tooth-identifying code for indicating the tooth number for which it is intended for use.

5. The device of claim 3, further including a securing material that is initially flowable to fit between the at least one protrusion and an opening in the coronal pontic portion, the securing material hardening to form the two-part gingival pontic device.

6. A fixed dental prosthesis for mimicking at least two natural teeth, comprising:
 a plurality of interconnected tooth-shaped portions, a first one of the interconnected tooth-shaped portions being a pontic device for fitting over an extraction site where a natural tooth has been extracted, a second one of the interconnected tooth-shaped portions including an internal surface for engaging at least one of a natural prepped tooth or an abutment coupled to a dental implant;
 wherein the pontic device is formed by a two-part pontic assembly comprising a gingival pontic portion and a coronal pontic portion, the gingival pontic portion including a generally curved, solid, uninterrupted dome-shaped structure having an anatomic shape for removably fitting within and preserving gingival tissue surrounding the extraction site, the coronal pontic portion being coupled to the gingival pontic portion and having a tooth shape.

7. The fixed dental prosthesis of claim 6, wherein the gingival pontic portion includes at least one protrusion extending coronally away from the gingival pontic portion, the coronal pontic portion fitting around the least one protrusion.

8. The fixed dental prosthesis of claim 7, further including a securing material that is initially flowable to fit between the protrusion and an opening in the coronal pontic portion, the securing material hardening to form the two-part pontic assembly.

9. The fixed dental prosthesis of claim 6, wherein the gingival pontic portion includes a concave coronal end, the coronal end having a perimeter that is configured to substantially correspond to and form a seal with the gingival tissue surrounding the extraction site.

10. The fixed dental prosthesis of claim 9, wherein the perimeter is asymmetrically scalloped with opposing distal and mesial peaks and opposing lingual and facial valleys between the peaks.

11. The fixed dental prosthesis of claim 6, wherein the plurality of interconnected tooth-shaped portions includes three interconnected tooth-shaped portions, a third one of the interconnected tooth-shaped portions including an interior surface for engaging another natural prepped tooth or another abutment coupled to another dental implant, the first one of the three interconnected tooth-shaped portions being located between the second one and the third one of the three interconnected tooth-shaped portions.

* * * * *